(12) United States Patent
Cao

(10) Patent No.: US 11,065,225 B1
(45) Date of Patent: Jul. 20, 2021

(54) ULTRA-LOW DOSE THC AS A POTENTIAL THERAPEUTIC AND PROPHYLACTIC AGENT FOR ALZHEIMER'S DISEASE

(71) Applicant: Chuanhai Cao, Tampa, FL (US)

(72) Inventor: Chuanhai Cao, Tampa, FL (US)

(73) Assignee: UNIVERSITY OF SOUTH FLORIDA, Tampa, FL (US)

(*) Notice: Subject to any disclaimer, the term of this patent is extended or adjusted under 35 U.S.C. 154(b) by 0 days.

(21) Appl. No.: 15/909,941

(22) Filed: Mar. 1, 2018

Related U.S. Application Data

(63) Continuation-in-part of application No. 15/225,351, filed on Aug. 1, 2016, now abandoned.

(60) Provisional application No. 62/198,921, filed on Jul. 30, 2015.

(51) Int. Cl.
*A61K 31/352* (2006.01)
*A61P 25/28* (2006.01)

(52) U.S. Cl.
CPC .......... *A61K 31/352* (2013.01); *A61P 25/28* (2018.01)

(58) Field of Classification Search
CPC combination set(s) only.
See application file for complete search history.

(56) References Cited

U.S. PATENT DOCUMENTS

2005/0031651 A1* 2/2005 Gervais .................. A61K 45/06
424/400

FOREIGN PATENT DOCUMENTS

WO WO-2016071819 A1 * 5/2016 .............. A61P 43/00

OTHER PUBLICATIONS

Singer et al. Sleep (2003) 26(7), p. 893-901.*
Campbell et al. British Journal of Pharmacology, (2007), 152, p. 655-662.*
FDA Drug Label of Marinol® (2004).*
Monmouth Medical Center, Synthetic Marijuana (dronabinol or Marinol®) reduces agitation in patients with Alzheimer's, Science Daily, Nov. 18, 2013.*
Eubanks et al., "A Molecular Link Between the Active Component of Marijuana and Alzheimer's Disease Pathology," Mol. Pharm., 2006, 3(6):773-777.
Walther et al., "Delta-9-tetrahydrocannabinol for nighttime agitation in severe dementia," Psychopharmacology (Berl) 185: 524-528 (2006).
Volicer et al., "Effects of dronabinol on anorexia and disturbed behavior in patients with Alzheimer's disease," Int J Geriatr Psychiatry, 12:913-919 (1997).

Agadjanyan et al., "Prototype Alzheimer's disease vaccine using the immunodominant B cell epitope from beta-amyloid and promiscuous T cell epitope pan HLA DR-binding peptide," J Immunol 174, 1580-1586 (2005).
Alzheimer's Association, "Alzheimer's disease facts and figures," Alzheimers Dement 8, 131-168 (2012).
Arendash et al. "Caffeine and coffee as therapeutics against Alzheimer's disease," J Alzheimers Dis 20 (Suppl 1), S117-S126 (2010).
Ashton et al., "Expression of the cannabinoid CB2 receptor in the rat cerebellum: An immunohistochemical study," Neurosci Lett, 396: 113-116 (2006).
Asuni et al., "GSK3alpha exhibits beta-catenin and tau directed kinase activities that are modulated," Wnt In. Eur J Neurosci, 24: 3387-3392 (2006).
Benito et al., "CB2 receptors and fatty acid amide hydrolase are selectively overexpressed in neuritic plaque-associated glia in Alzheimer's disease brains," J Neurosci, 23: 11136-11141 (2003).
Bisogno et al., "Cannabinoid receptors and endocannabinoids: Role in neuroinflammatory and neurodegenerative disorders," CNS Neural Disord Drug Targets, 9: 564-573 (2010).
Brookmeyer, "Forecasting the global burden of Alzheimer's disease," Alzheimers Dement 3, 186-191 (2007).
Van Sickle et al., "Identification and functional characterization of brainstem cannabinoid CB2 receptors," Science, eoo5, 310:329-332 (2005).
Cao et al., "Caffeine suppresses amyloid-beta levels in plasma and brain of Alzheimer's disease transgenic mice," J Alzheimers Dis, 17: 681-697 (2009).
Cao et al., "High blood caffeine levels in MCI linked to lack of progression to dementia," J Alzheimers Dis 30, 559-572 (2012).
Chiti et al., "Protein misfolding, functional amyloid, and human disease," Annu Rev Biochem 75, 333-366 (2006).
Cho et al., "Glycogen synthase kinase 3beta phosphorylates tau at both primed and unprimed sites," Differential impact on microtubule binding. J Biol Chem., 278: 187-193 (2003).
Darocha-Souto et al., "Activation of glycogen synthase kinase-3 beta mediates beta-amyloid induced neuritic damage n Alzheimer's disease," Neurobiol Dis_45: 425-437 (2012).
Dragicevic et al., "Melatonin treatment restores mitochondrial function in Alzheimer's mice:Amitochondrial protective role of melatonin membrane receptor signaling," J Pineal Res 51, 75-86 (2011).
Engel et al., "Chronic lithium administration to FTDP-17 tau and GSK-3beta overexpressing mice prevents tau riyperphosphorylation and neurofibrillary tangle formation," but pre-formed neurofibrillary tangles do not revert. J Neurochem, 99: 1445-1455 (2006).
Fishbein et. al., "Long-term behavioral and biochemical effects of an ultra-low dose of .l'i.9-tetrahydrocannabinol (THC): heuroprotection and ERK signaling," Exp Brain Res, 221(4):437-438 (2012).

(Continued)

*Primary Examiner* — Kortney L. Klinkel
*Assistant Examiner* — Tori Strong
(74) *Attorney, Agent, or Firm* — Michael Best & Friedrich LLP

(57) ABSTRACT

Alzheimer's disease is treated using THC (alone, or in combination with melatonin) administered in an ultra-low dose amount sufficient to (i) reduce Aß expression; (ii) reduce Aß aggregation: (iii) maintain APP expression; (iv) enhance mitochondrial functioning; (v) decrease phosphorylation of GSK3ß protein; (vi) decrease the expression of GSK3ß protein; (vii) decrease phosphorylation of Tau protein; and/or (viii) maintain Tau protein expression, in said patient without severe psychological impairments and side effects associated with higher doses of THC.

4 Claims, 31 Drawing Sheets

(56) References Cited

OTHER PUBLICATIONS

Gotz et al., Modes of A-toxicity in Alzheimer's disease. Cell Mal Life Sci 68, 3359-3375 (2011).
Hanger et al., "Glycogen synthase kinase-3 induces Alzheimer's disease-like phosphorylation of tau: Generation of paired helical filament epitopes and neuronal localisation of the kinase," Neurosci Lett., 147: 58-62 (1992).
Hernandez et al., "GSK3 and tau: Two convergence points in Alzheimer's disease," J Alzheimers Dis., 33 (Suppl 1): S141-S144 (2013).
Hooper et al., "The GSK3 hypothesis of Alzheimer's disease," J Neurochem, 104: 1433-1439 (2008).
Ishiguro et al., "Phosphorylation sites on tau by tau protein kinase I, a bovine derived kinase generating an epitope of paired helical filaments," Neurosci Lett., 148: 202-206 (1992).
Jackson et al., "Cannabinoids and neuroprotection in CNS inflammatory disease," J Neurol Sci., 233:21-25 (2005).
Lovestone et al., "Alzheimer's disease-like phosphorylation of the microtubule-associated protein tau by glycogen synthase kinase-3 in transfected mammalian cells," Curr Biol., 4: 1077-1086 (1994).
Marchalant et al., "Cannabinoids attenuate the effects of aging upon neuroinflammation and neurogenesis," Neurobiol Dis, 34: 300-307 (2009).
Martin-Moreno et al., "Cannabidiol and other cannabinoids reduce microglial activation in vitro and in vivo: Relevance o Alzheimer's disease," Mol Pharmacol, 79: 964-973 (2011).
Mishra et al., "Tetrahydrocurcumin confers protection against amyloid 13-induced toxicity," Neuroreport, 22: 23-27 (2011).
Nakamura et al., "Reversible effects of acute and long-term administration of delta-9-tetrahydrocannabinol (THC) on memory in the rat," Drug Alcohol Depend, 28(2): 167-175 (1991).
Nunez et al., "Cannabinoid CB2 receptors are expressed by perivascular microglial cells in the human brain: An immunohistochemical study," Synapse, 53: 208-213 (2004).
Octave, "The amyloid peptide and its precursor in Alzheimer's disease," Rev Neurosci, 6: 287-316 (1995).
Phiel et al., "GSK-3alpha regulates production of Alzheimer's disease amyloid-beta peptides," Nature. 2003; J23: 435-439 (2003).
Pillay et al., "Molecular mechanisms, emerging etiological insights and models to test potential therapeutic interventions in Alzheimer's disease," Curr Alzheimer Res 1: 295-306 (2004).
Piomelli, "The molecular logic of endocannabinoid signalling," Nat Rev Neurosci 4, 873-884 (2003).
Proctor et al., "GSK3 and p53—is there a link in Alzheimer's disease?," Mol Neurodegener, 5:7 (2010).
Ramirez et al., "Prevention of Alzheimer's disease pathology by cannabinoids: Neuroprotection mediated by blockade of microglial activation," J Neurosci, 25: 1904-1913 (2005).
Reitz et al., "Epidemiology of Alzheimer disease," Nat Rev Neural, 7:137-152 (2011).
Rich et al., "Nonsteroidal anti-inflammatory drugs in Alzheimer's disease," Neurology 45, 51-55 (1995).
Riedel et al., "Cannabinoid function in learning, memory and plasticity," Handb Exp Pharmacol, pp. 445-477 (2005).
Saxena, "Bioenergetics breakdown in Alzheimer's disease: Targets for new therapies," Int J Physiol Pathophysiol Pharmacol 3, 133-139 (2011).
Sun et al., "Lithium inhibits amyloid secretion in COS7 cells transfected with amyloid precursor protein C100," Neurosci e-ett, 321:61-64 (2002).
Athanasiou et al., "Cannabinoid receptor agonists are mitochondrial inhibitors: a unified hypothesis of how cannabinoids modulate mitochondrial function and induce cell death," Biochem Biophys Res Commun, 2007, 364(1):131-137.
Avila et al., "Tau aggregation into fibrillar polymers: taupathies," FEBS Lett, 2000, 476: 82-92.
Costa et al., "Changes in rat brain energetic metabolism after exposure to anandamide or $\Delta^9$-tetrahydrocannabinol," European Journal of Pharmacology, 2000, 395:1-7.
Demuro et al., "The absolute bioavailability of oral melatonin," J Clin Pharmacol, 2000, 40(7): 781-784.
Deng et al., "Effects of melatonin on wortmannin-induced tau hyperphosphorylation," Acta Pharmacologica Sinica, 2005, 26: 519-526.
Esposito et al., "The marijuana component cannabidiol inhibits beta-amyloid-induced tau protein hyperphosphorylation through Wnt/beta-catenin pathway rescue in PC12 cells," J Mol Med (Berl), 2006,84(3):253-258.
Feng et al., "Melatonin alleviates behavioral deficits associated with apoptosis and cholinergic system dysfunction in the APP 695 transgenic mouse model of Alzheimer's disease," J Pineal Res, 2004, 37(2):129-136.
Garcia-Mesa et al., "Melatonin plus physical exercise are highly neuroprotective in the 3xTg-AD mouse," Neurobiol Aging, 2012, 33(6):1124.e13-1124.e29.
Hoppe et al., "Amyloid-beta neurotoxicity in organotypic culture is attenuated by melatonin: involvement of GSK-3ß, tau and neuroinflammation," J Pineal Res, 2010, 48(3):230-238.
Ionov et al., "Mechanism of neuroprotection of melatonin against beta-amyloid neurotoxicity," Neuroscience, 2011, 180:229-237.
Li et al., "Melatonin protects SH-SY5Y neuroblastoma cells from calyculin A-induced neurofilament impairment and neurotoxicity," J Pineal Res, 2004, 36: 186-191.
Mansouri et al., "An alcoholic binge causes massive degradation of hepatic mitochondrial DNA in mice," Gastroenterology, 1999, 117(1):181-190.
Martin et al., "Melatonin-induced increased activity of the respiratory chain complexes I and Iv can prevent mitochondrial damage induced by ruthenium red in vivo," J. Pinea. Res., 2000, 28:242-248.
Matsubara et al., "Melatonin increases survival and inhibits oxidative and amyloid pathology in a transgenic model of Alzheimer's disease," J Neurochem, 2003, 85(5):1101-1108.
Maurizi et al., "The mystery of Alzheimer's disease and its prevention by melatonin," Med Hypotheses, 1995, 45(4):339-340.
McGilveray, "Pharmacokinetics of cannabinoids," Pain Res Manag, 2005, 10, Sppl. A: 15A-22A.
Ng et al., "Melatonin reduces hippocampal beta-amyloid generation in rats exposed to chronic intermittent hypoxia," Brain Res, 2010, 1354:163-171.
Olcese et al., "Protection against cognitive deficits and markers of neurodegeneration by longterm oral administration of melatonin in a transgenic model of Alzheimer disease," J Pineal Res, 2009, 47(1):82-96.
Olivieri et al., "Melatonin protects SHSY5Y neuroblastoma cells from cobalt-induced oxidative stress, neurotoxicity and increased beta-amyloid secretion," J Pineal Res, 2001, 31(4):320-325.
O'Neal-Moffitt et al., "Prophylactic melatonin significantly reduces Alzheimer's neuropathology and associated cognitive deficits independent of antioxidant pathways in AβPPswe/PS1 mice," Mol Neurodegener, 2015, 10:27.
Ozaita et al., "Regulation of PI3K/Akt/GSK-3 pathway by cannabinoids in the brain," J Neurochem, 2007, 102(4):1105-1114.
Pappolla et al., "Inhibition of Alzheimer's β-fibrillogenesis by melatonin," Jour. of Biological Chemistry, 1998, 273(13):7185-7188.
Poeggeler et al., "Melatonin Reverses the Profibrillogenic Activity of Apolipoprotein E4 on the Alzheimer Amyloid Aβ Peptide," Biochemistry, 2001, 40(49):14995-15001.
Priller et al., "Synapse formation and function is modulated by the amyloid precursor protein," The Journal of Neuroscience, 2006, 26(27):7212-7221.
Randall et al., "The functional neurophysiology of the amyloid precursor protein (APP) processing pathway," Neuropharmacology, 2010, 59(4-5):243-267.
Roch et al., "Increase of synaptic density and memory retention by a peptide representing the trophic domain of the amyloid ß/A4 protein precursor," Proc Natl Acad Sci USA, 1994, 91(16):7450-7454.

(56) References Cited

OTHER PUBLICATIONS

Rudnitskaya et al., "Melatonin Attenuates Memory Impairment, Amyloid-β Accumulation, and Neurodegeneration in a Rat Model of Sporadic Alzheimer's Disease," J Alzheimers Dis, 2015, 47(1):103-116.

Song et al., "Melatonin alters the metabolism of the beta-amyloid precursor protein in the neuroendocrine cell line PC12," J Molecular Neuroscience, 1997, 9(2): 75-92.

Wang et al., "Effect of melatonin and melatonylvalpromide on beta-amyloid and neurofilaments in N2a cells," Neurochem Res, 2008, 33(6):1138-1144.

Wang et al., "Melatonin ameliorated okadaic-acid induced Alzheimer-like lesions," Acta Pharmacologica Sinica, 2004, 25: 276-280.

Wang et al., "Melatonin attenuates isoproterenol-induced protein kinase A over activation and tau hyperphosphorylation in rat brain," J Pineal Res, 2004, 37: 11-16.

Anderson et al., "Reduced cerebrospinal fluid levels of α-secretase-cleaved amyloid precursor protein in aged rats: correlation with spatial memory deficits," Neuroscience, 1999, 93(4):1409-1420.

Casarejos et al., "Natural Cannabinoids Improve Dopamine Neurotransmission and Tau and Amyloid Pathology in a Mouse Model of Tauopathy," Journal of Alzheimer's Disease, 2013, 35:525-539.

Guennewig et al., "THC exposure of human iPSC neurons impacts genes associated with neuropsychiatric disorders," Translational Psychiatry, 2018, 8:89, 9 pages.

Hurtado et al., "Selectively Silencing GSK-3 Isoforms Reduces Plaques and Tangles in Mouse Models of Alzheimer's Disease," The Journal of Neuroscience, 2012, 32(21):7392-7402.

Lannfelt et al., "Decreased α-secretase-cleaved amyloid precursor protein as a diagnostic marker for Alzheimer's disease," Nature Medicine, 1995, 1(8):829-832.

Lew, "Tau protein after delta-9-tetrahydrocannabinol in a human neuroblastoma cell line," Gen. Pharmac., 1996, 27(7):1141-1143.

Pasciuto et al., "Dysregulated ADAM10-Mediated Processing of APP during a Critical Time Window Leads to Synaptic Deficits in Fragile X Syndrome," Neuron, 2015, 87(2):382-398.

Reddy et al., "Abnormal mitochondrial dynamics and synaptic degeneration as early events in Alzheimer's disease: implications to mitochondria-targeted antioxidant therapeutics," Biochim Biophys Acta, 2012, 1822(5):639-649.

Ring et al., "The secreted β-amyloid precursor protein ectodomain APPsα is sufficient to rescue the anatomical, behavioral, and electrophysiological abnormalities of APP-deficient mice," The Journal of Neuroscience, 2007, 27(29):7817-7826.

Sarafian et al., "Δ9-Tetrahydrocannabinol disrupts mitochondrial function and cell energetics," Am J Physiol Lung Cell Mol Physiol, 2003, 2884:L298-L306.

Selkoe, "Alzheimer's Disease: Genes, Proteins, and Therapy," Physiological Reviews, 2001, 81(2):741-766.

Shahani et al., "Functions and malfunctions of the tau proteins," CMLS, Cell Mol Life Sci, 2002, 59:1668-1680.

Swerdlow, "Brain aging, Alzheimer's disease, and mitochondria," Biochim Biophys Acta, 2011, 1812(12):1630-1639.

Zhu et al., "Abnormal Mitochondrial Dynamics in the Pathogenesis of Alzheimer's Disease," J Alzheimers Dis, 2013, 33(01):S253-S262.

United States Patent Office Action for U.S. Appl. No. 15/225,351 dated Feb. 8, 2017 (12 pages).

United States Patent Office Action for U.S. Appl. No. 15/225,351 dated Sep. 1, 2017 (16 pages).

* cited by examiner

ULTRA-LOW DOSE THC AS A POTENTIAL THERAPEUTIC AND PROPHYLACTIC AGENT FOR ALZHEIMER'S DISEASE

CROSS-REFERENCE TO RELATED APPLICATION(S)

This application claims priority to U.S. Provisional Patent Application No. 62/198,921, filed on Jul. 30, 2015, and is a continuation-in-part of co-pending application U.S. patent application Ser. No. 15/225,351, filed on Aug. 1, 2016, each of which are incorporated herein by reference in their entirety.

TECHNICAL FIELD

This invention relates to treatment of Alzheimer's disease. More specifically, the present invention provides therapeutic methods and compositions for treating Alzheimer's disease.

BACKGROUND

Alzheimer's disease (AD) is one of the most common neurodegenerative disorders worldwide. In 2011 alone, 15 million family members have provided more than 17.4 billion hours of care to diagnosed Alzheimer's disease (AD) patients. That care translates into more than $210 billion of AD-related services (Alzheimer's, Assn, 2012 Alzheimer's disease facts and figures. Alzheimer's Dement. 2012; 8: 131-168). This disease translates into an enormous burden on caregivers, as well as the health care system, both medically and economically. To date, there have been no effective treatments developed to cure or delay the progression of AD (Saxena, Bioenergetics breakdown in Alzheimer's disease: Targets for new therapies. Int J Physiol Pathophysiol Pharmacol. 2011; 3: 133-139; Götz, et al., Modes of Aβ toxicity in Alzheimer's disease. Cell Mol Life Sci. 2011; 68: 3359-3375). By 2050, an estimated 11 to 16 million Americans will be living with the disease (Alzheimer's, Assn, 2012 Alzheimer's disease facts and figures. Alzheimer's Dement. 2012; 8: 131-168; Brookmeyer, et al, Forecasting the global burden of Alzheimer's disease. Alzheimers Dement. 2007; 3: 186-191).

AD pathology can be divided into two categories, familial inherited AD and sporadic AD. The histopathologies of early onset familial AD and late onset sporadic AD are indistinguishable. Both forms of AD are characterized by extracellular amyloid-β (Aβ) plaques and intracellular tau-containing neurofibrillary tangles (Götz, et al., Modes of Aβ toxicity in Alzheimer's disease. Cell Mol Life Sci. 2011; 68: 3359-3375). The misfolded structure of the Aβ peptides, along with neurofibrillary tangles, generates a characteristic tendency for their aggregation (Chiti & Dobson, Protein misfolding, functional amyloid, and human disease. Annu Rev Biochem. 2006; 75: 333-366) around damaged or dead neurons and within cerebral vasculature in the brain. It manifests by memory loss followed by progressive dementia.

It has long been believed that Aβ1-40 (Aβ40) and Aβ1-42 (Aβ42) aggregates are the constituents of the insoluble plaques that are characteristic of AD. This disease is also associated with neuroinflammation, excitotoxicity, and oxidative stress (Campbell & Gowran, Alzheimer's disease; taking the edge off with cannabinoids? Br J Pharmacol. 2007; 152: 655-662; Rich, et al., Nonsteroidal anti-inflammatory drugs in Alzheimer's disease. Neurology. 1995; 45: 51-55). However, the continuous aggregation of Aβ peptides along with hyperphosphorylation of the tau protein inside the cell, causing neurofibrillary tangle formation, are generally accepted as the major etiological factors of the neuronal cell death associated with the progression of AD (Octave, The amyloid peptide and its precursor in Alzheimer's disease. Rev Neurosci. 1995; 6: 287-316; Reitz, et al., Epidemiology of Alzheimer disease. Nat Rev Neurol. 2011; 7: 137-152; Pillay, et al., Molecular mechanisms, emerging etiological insights and models to test potential therapeutic interventions in Alzheimer's disease. Curr Alzheimer Res. 2004; 1: 295-306).

The studies provide evidence that Aβ peptides are neurotoxic, as they are reported mediators of apoptosis, inflammation, and oxidative stress. For this reason, some of the earliest proposed therapeutic strategies entail the prevention or elimination of these Aβ peptides and subsequent formation of toxic oligomers. Aβ peptides are produced via the amyloidogenic pathway of amyloid precursor protein (APP) proteolysis, which involves the concerted effort of β- and γ-secretases. Initially, β-secretase (BACE) cleaves APP, creating an Aβ-containing carboxyl-terminal fragment known as β-C-terminal fragment (β-CTF), or C99 and an amino-terminal, soluble APP-β (sAPP-β) fragment, which is released extracellularly. Intracellularly, the β-CTF fragment is then cleaved by a multiprotein γ-secretase complex, resulting in generation of the Aβ peptide and a smaller γ-CTF, also known as C57. Aβ is known to increase: cellular Ca2+, mitochondrial dysfunction, generation of reactive oxygen species, and neuronal cell death by apoptosis or necrosis.

Recent studies have also suggested that glycogen synthase kinase 3 (GSK-3) has a key role in the pathogenesis of both sporadic and familial AD (Hooper, et al., The GSK3 hypothesis of Alzheimer's disease. J Neurochem. 2008; 104: 1433-1439; Proctor & Gray, GSK3 and p53—is there a link in Alzheimer's disease? Mol Neurodegener. 2010; 5: 7). It has been reported that GSK-3β induces hyperphosphorylation of tau (Lovestone, et al., Alzheimer's disease-like phosphorylation of the microtubule-associated protein tau by glycogen synthase kinase-3 in transfected mammalian cells. Curr Biol. 1994; 4: 1077-1086; Ishiguro, et al., Phosphorylation sites on tau by tau protein kinase I, a bovine derived kinase generating an epitope of paired helical filaments. Neurosci Lett. 1992; 148: 202-206; Hanger, et al., Glycogen synthase kinase-3 induces Alzheimer's disease-like phosphorylation of tau: Generation of paired helical filament epitopes and neuronal localization of the kinase. Neurosci Lett. 1992; 147: 58-62; Cho & Johnson, Glycogen synthase kinase 3beta phosphorylates tau at both primed and unprimed sites. Differential impact on microtubule binding. J Biol Chem. 2003; 278: 187-193; Asuni, et al., GSK3alpha exhibits beta-catenin and tau directed kinase activities that are modulated by Wnt In. Eur J Neurosci. 2006; 24: 3387-3392). Moreover, overexpression of GSK-3 in Tet/GSK-3β mice reveal pathological symptoms that correspond to AD pathology with respect to spatial learning deficits, reactive astrocytosis, increased Aβ production, and plaque associated inflammation, as well as tau hyperphosphorylation resulting in Aβ-mediated neuronal death (Hernandez, et al., GSK3 and tau: Two convergence points in Alzheimer's disease. J Alzheimers Dis. 2013; 33(Suppl 1): S141-S144). Additionally, chronic lithium (GSK-3 inhibitor) treatment in double transgenic mice overexpressing GSK-3β and tau has shown to prevent tau hyperphosphorylation and neurofibrillary tangle formation (Engel, et al., Chronic lithium administration to FTDP-17 tau and GSK-3beta overexpressing mice prevents tau hyperphosphorylation and neurofibrillary tangle formation, but pre-formed neurofibrillary tangles do not revert. J Neurochem. 2006; 99: 1445-1455). Some reports have also indicated that GSK-3α plays a role in regulating amyloid-β protein precursor (AβPPP) cleavage, resulting in increased Aβ production (Phiel, et al., (2003) GSK-3alpha regulates production of Alzheimer's disease amyloid-beta peptides. Nature. 2003; 423: 435-439; Sun, et al., Lithium inhibits amyloid secretion in COS7 cells transfected with amyloid precursor protein C100. Neurosci Lett. 2002; 321: 61-64). It has also been shown that the Aβ load in mouse brain can be robustly ameliorated by the inhibition of GSK-3β (DaRocha-Souto, et al., Activation of glycogen synthase kinase-3 beta mediates beta-amyloid induced neuritic damage in Alzheimer's disease. Neurobiol Dis. 2012; 45: 425-437).

Along with past research suggesting an involvement of GSK-3 in the pathogenesis of AD, there has also been recent studies suggesting the intricate involvement of the cannabinoid system in AD. It was reported that the cannabinoid system can limit the neurodegenerative processes that drive the progression of the disease, and may provide a new avenue for disease control (Jackson, et al., Cannabinoids and neuroprotection in CNS inflammatory disease. J Neurol Sci. 2005; 233: 21-25). Currently the complete pathway and mechanism of action of the cannabinoid system are unknown, however, studies have been conducted to determine the involvement of the cannabinoid 1 (CB1) and cannabinoid 2 (CB2) receptors in AD brain (Campbell & Gowran, Alzheimer's disease; taking the edge off with cannabinoids? Br J Pharmacol. 2007; 152: 655-662). The CB1 receptor is abundant in the brain and contributes to learning, memory, and cognitive processes which are interrupted early in the course of AD on set (Riedel & Davies, Cannabinoid function in learning, memory and plasticity. Handb Exp Pharmacol. 2005; 445-477). To the contrary, CB2 receptor expression is more limited and has been anatomically found in neurons within the brainstem (Van Sickle, et al., Identification and functional characterization of brainstem cannabinoid CB2 receptors. Science. 2005; 310: 329-332), cerebellum (Ashton, et al., Expression of the cannabinoid CB2 receptor in the rat cerebellum: An immunohistochemical study. Neurosci Lett. 2006; 396: 113-116), and microglia (Nunez, et al., Cannabinoid CB2 receptors are expressed by perivascular microglial cells in the human brain: An immunohistochemical study. Synapse. 2004; 53: 208-213). Recent research has also investigated the propensity of endocannabinoid receptor sub-types 1 (CB1) and 2 (CB2) to elicit a neuroprotective and anti-inflammatory effect on the brain when stimulated by endocannabinoids (Marchalant, et al., Cannabinoids attenuate the effects of aging upon neuroinflammation and neurogenesis. Neurobiol Dis. 2009; 34: 300-307). Postmortem studies of AD brains have detected increased expression of CB1 and CB2 receptors on microglia within the plaque, while CB1 expression is reduced in neurons more remote from the plaque (Ramírez, et al., Prevention of Alzheimer's disease pathology by cannabinoids: Neuroprotection mediated by blockade of microglial activation. J Neurosci. 2005; 25: 1904-1913). It is also noted that the endocannabinoid metabolizing enzyme, fatty acid amide hydrolase, is upregulated in the plaque (Benito, et al., Cannabinoid CB2 receptors and fatty acid amide hydrolase are selectively overexpressed in neuritic plaque-associated glia in Alzheimer's disease brains. J Neurosci. 2003; 23: 11136-11141). There is also an increase in expression of anandamide metabolites, such as arachidonic acid, in the vicinity of the plaque (Benito, et al., Cannabinoid CB2 receptors and fatty acid amide hydrolase are selectively overexpressed in neuritic plaque-associated glia in Alzheimer's disease brains. J Neurosci. 2003; 23: 11136-11141). These findings may indirectly suggest that the increase in CB1 and CB2 receptors may be to offset the lack of activity with their ligands due to increased metabolic activity of fatty acid amide hydrolase. These alterations in the cannabinoid system suggest an involvement of endogenous cannabinoids in the pathogenesis of AD or that this system may be altered by the pathophysiology of the disease (Campbell & Gowran, Alzheimer's disease; taking the edge off with cannabinoids? Br J Pharmacol. 2007; 152: 655-662). Understanding that microglial activation is reserved in all cases of AD, it is important to identify that endogenous cannabinoids prevent Aβ-induced microglial activation both in vitro and in vivo (Martin-Moreno, et al., Cannabidiol and other cannabinoids reduce microglial activation in vitro and in vivo: Relevance to Alzheimer's disease. Mol Pharmacol. 2011; 79: 964-973). These receptors are known to experience time-dependent and brain region specific alterations during neurodegenerative and neuroinflammatory disorders to attempt to counteract excitotoxicity and inflammation (Bisogno & Di Marzo, Cannabinoid receptors and endocannabinoids: Role in neuroinflammatory and neurodegenerative disorders. CNS Neurol Disord Drug Targets. 2010; 9: 564-573).

Endocannabinoid receptors, CB1 and CB2, have been reported to interact with the endocannabinoid molecules: 2-arachidonoyl glycerol and anandamide. However, it has also been reported that CB1 and CB2 also interact with Δ9-tetrahydrocannabinol (THC) isolated from the *Cannabis sativa* plant (Piomelli, The molecular logic of endocannabinoid signalling. Nat Rev Neurosci. 2003; 4: 873-884). Furthermore, early reports indicate that Dronabinol, an oil-based solution of Δ9-THC, improves the disturbed behavior and stimulates appetite in AD patients (Volicer, et al., Effects of dronabinol on anorexia and disturbed behavior in patients with Alzheimer's disease. Int J Geriatr Psychiatry. 1997; 12: 913-919), and alleviates nocturnal agitation in severely demented patients (Walther, et al., Delta-9-tetrahydrocannabinol for nighttime agitation in severe dementia. Psychopharmacology (Berl). 2006; 185: 524-528). Accumulated evidence also suggests antioxidants having anti-inflammatory and neuroprotective roles (Jackson, et al., Cannabinoids and neuroprotection in CNS inflammatory disease. J Neurol Sci. 2005; 233: 21-25).

SUMMARY OF THE INVENTION

This invention provides a method for treating Alzheimer's disease which includes administering tetrahydrocannabinol (THC) to a patient suffering from Alzheimer's disease. THC is administered in an ultra-low dose amount sufficient to: (i) reduce Aβ expression; (ii) reduce Aβ aggregation; (iii) enhance mitochondrial functioning; (iv) decrease phosphorylation of GSK3β protein; (v) decrease the expression of GSK3β protein; and/or (vi) decrease Tau protein expression in said patient without severe psychological impairments and side effects associated with higher doses of THC.

In a further embodiment, THC is administered in an amount of at least 0.2 µg/kg of body weight of a patient but less than the amount that causes psychological impairments and side effects associated with higher doses of THC. In other further embodiments, THC is administered in an amount of from about 0.2 µg/kg to about 0.16 mg/kg of body weight of the patient, and preferably in an amount of from about 0.2 µg/kg to about 0.02 mg/kg of body weight of the patient.

The invention also provides a composition for treating Alzheimer's disease which includes THC in an ultra-low dose amount sufficient to: (i) reduce Aß expression; (ii) reduce Aß aggregation; (iii) enhance mitochondrial functioning; (iv) decrease phosphorylation of GSK3ß protein; (v) decrease the expression of GSK3ß protein; and/or (vi) decrease Tau protein expression in said patient without severe psychological impairments and side effects associated with higher doses of THC.

In a further embodiment of the method, Alzheimer's disease patients are treated with a composition of THC and melatonin wherein THC is administered in an ultra-low dose amount sufficient to: (i) reduce Aß expression; (ii) reduce Aß aggregation: (iii) maintain APP expression; (iv) enhance mitochondrial functioning; (v) decrease phosphorylation of GSK3ß protein; (vi) decrease the expression of GSK3ß protein; (vii) decrease phosphorylation of Tau protein; and/ or (viii) maintain Tau protein expression in said patient without severe psychological impairments and side effects associated with higher doses of THC, and melatonin is administered with THC wherein the ratio of THC:melatonin is from about 1:400 to about 1: 4000.

In a further embodiment, THC is administered with melatonin in an amount of at least 0.2 µg/kg of body weight of a patient but less than the amount that causes more severe psychological impairments and more severe side effects associated with higher doses of THC. Melatonin is administered with THC in amounts of about 0.11 mg/kg to about 1.1 mg/kg.

In a further embodiment, of the method, Alzheimer's disease patients are treated with a composition of THC and melatonin wherein THC is administered in an ultra-low dose amount such that the combination is sufficient to in an Alzheimer's patient; without severe psychological impairments and severe side effects associated with higher doses of THC and melatonin is administered with THC wherein the ratio of THC to melatonin is from about 1:400 to about 1:4000.

DESCRIPTION OF THE DRAWINGS

For a fuller understanding of the invention, reference should be made to the following detailed description, taken in connection with the accompanying drawings, in which.

Figure 1A:
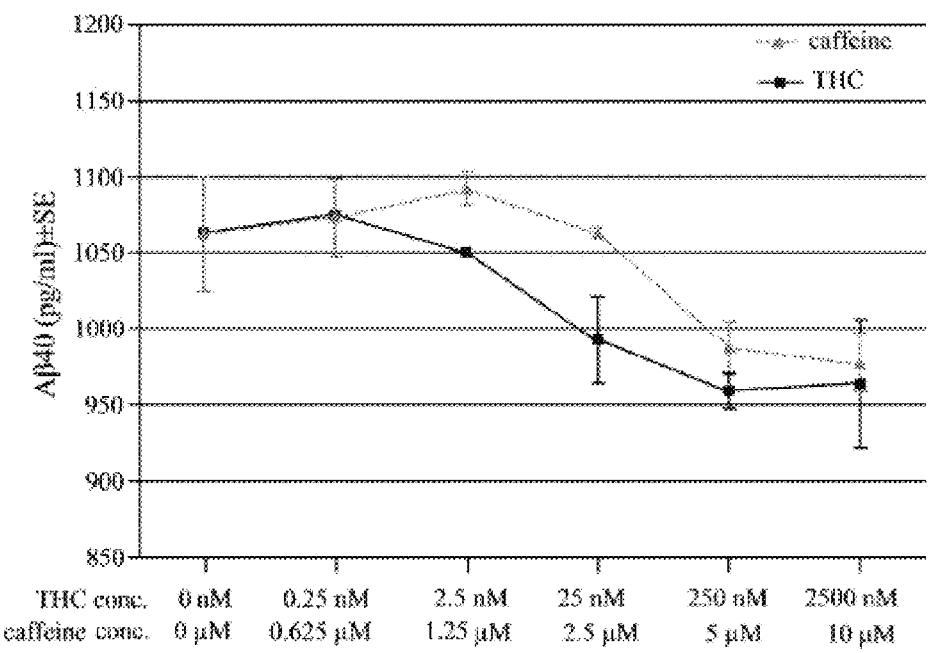
FIG. 1A is a graph of N2a/AβPPswe cells showing Aβ40 (pg/ml) levels in vitro, measured 6 hours from incubation. Cells were either not treated, treated with THC, or treated with caffeine as a positive control. Treatment with THC results in a dose-dependent decrease in Aβ40 production after 6 hours.

In connection with FIGS. 5C, 5D, 6A, 6B, 6C, 6D, 7, 8, 10A, 10B, 11A, 11B, 11C, 11D, 12, 13, 14A and 14B, see the following table:

| Description of Legends on Figures | | |
| --- | --- | --- |
| Legend | THC | Melatonin |
| T1 | 25 nM | |
| T2 | 2.5 nM | |
| T3 | 0.25 nM | |

-continued

Description of Legends on Figures

| Legend | THC | Melatonin |
|---|---|---|
| M1 | | 10-5M |
| M2 | | 10-6M |
| M1T2 | 2.5 nM | 10-5M |
| M2T2 | 2.5 nM | 10-6M |

DETAILED DESCRIPTION

Described herein are results of investigations into the neuroprotective properties of a) ultra-low doses of THC, the active component of marijuana, and b) ultra-low doses of THC in combination with melatonin. The following were evaluated 1) the effects of ultra-low dose of THC and ultra-low dose THC in combination with melatonin against AβPP expression and against Aβ40 expression in N2a/AβPPswe cells; 2) the direct effects of ultra-low dose of THC on Aβ aggregation, one pathological marker of AD; 3) the effect of ultra-low dose of THC on mitochondrial function in N2a/AβPPswe cells; 4) the toxicity of ultra-low dose of THC; 5) the effects of ultra-low dose THC, and ultra-low dose THC in combination with melatonin on the phosphorylation of GSK-3β; 6) the effect of ultra-low dose THC on the protein expression of GSK-3β; and 7) the effects of ultra-low dose THC, in combination with melatonin on the total tau protein expression and phosphorylation of tau. These investigations culminated in the present invention, which includes a method for treating Alzheimer's disease, whereby tetrahydrocannabinol (THC) and the combination of THC and melatonin is administered to a patient suffering from Alzheimer's disease. THC is administered in an ultra-low dose amount sufficient to (i) reduce Aß expression; (ii) reduce Aß aggregation; (iii) maintain APP expression; (iv) enhance mitochondrial functioning; (v) decrease phosphorylation of GSK3ß protein; (vi) decrease the expression of GSK3ß protein; (vii) decrease phosphorylation of Tau protein; and/or (viii) decrease Tau protein expression in the patient with Alzheimer's without severe psychological impairments and side effects commonly associated with higher doses of THC.

1. DEFINITIONS

As used herein, the singular forms "a," "an" and "the" include plural referents unless the context clearly dictates otherwise. Thus, for example, reference to "a polypeptide" includes a mixture of two or more polypeptides and the like.

As used herein, "about" means approximately or nearly and in the context of a numerical value or range set forth means ±15% of the numerical.

As used herein "animal" means a multicellular, eukaryotic organism classified in the kingdom Animalia or Metazoa. The term includes, but is not limited to, mammals. Non-limiting examples include rodents, aquatic mammals, domestic animals such as dogs and cats, farm animals such as sheep, pigs, cows and horses, and humans. Wherein the terms "animal" or "mammal" or their plurals are used, it is contemplated that it also applies to any animals.

As used herein the term "patient" is understood to include an animal, especially a mammal, and more especially a human that is receiving or intended to receive treatment.

As used herein, the term "therapeutically effective amount" refers to that amount of a therapy (e.g., a chemotherapeutic agent) sufficient to result in the amelioration of Alzheimer's disease or other neurodegenerative disorder or one or more symptoms thereof, prevent advancement of Alzheimer's disease or other neurodegenerative disorder, or cause regression of Alzheimer's disease or other neurodegenerative disorder.

As used herein, "treating" means lessening the effects disease. In specific embodiments, treating means preventing or alleviating (reducing or eliminating) a symptom in a patient when administered one or more times over a suitable time period.

As used herein "an ultra-low dose" of THC shall mean an amount of THC which is sufficient to bring about one or more of the following effects in an Alzheimer's patient: (i) reduce Aß expression; (ii) reduce Aß aggregation; (iii) maintain APP expression; (iv) enhance mitochondrial functioning; (v) decrease phosphorylation of GSK3ß protein; (vi) decrease the expression of GSK3ß protein; (vii) decrease phosphorylation of Tau protein; and/or (viii) decrease Tau protein expression in a patient with Alzheimer's without severe psychological impairments and side effects associated with higher doses of THC.

As used herein "psychological impairments and side effects" shall mean undesirable effects observed in patients receiving THC in dose amounts of about 3 mg/kg and greater including feeling high, a decrease in mitochondrial function, a decrease in APP protein levels, anxiety, paranoia, hippocampal neuronal loss and similar effects.

2. EXAMPLES

Materials and Methods

Aβ40 levels in N2a/AβPPswe cells were determined after treatment with tetrahydrocannabinol (THC) or caffeine—a compound reported to lower serum Aβ40 levels in a mouse model (Cao, et al., Caffeine suppresses amyloid-beta levels in plasma and brain of Alzheimer's disease transgenic mice. J Alzheimers Dis. 2009; 17: 681-697).

N2a/AβPPswe cells (Samuel Gandy, Mount Sinai School of Medicine, NY, NY), N2a cells stably expressing human AβPP carrying the K670N/M671L Swedish mutation (AβPPswe), were grown in Dulbecco's modified Eagle medium containing 10% fetal bovine serum, 100 U/mL penicillin, 100 μg/mL streptomycin, and 400 μg/mL G418 (Invitrogen), at 37° C. in the presence of 5% CO2. N2a/AβPPswe cells were diluted with medium to a concentration of $2\times10^5$/ml, and plated into the each well in 3 ml. 2 ml of trypsin was incubated at room temperature, or 37° C. When most of the cells began to float, trypsin was decanted and 5 ml of fresh pre-warmed medium was added. Pipetting was performed more than 30 times to ensure cells were separated into individual cells. One drop of medium was put into 1.5 ml tubes for counting; 10 μl of trypan blue and 10 μl of medium of cells were added and applied to cytometer for counting. The rule was total number of cells of all for diagonal blocks/4×2×10000=number of cells/ml. The proper amount of cell medium and fresh medium was added into new flasks according to the ratio of dilution. Pipetting was performed 10 times to homogenize cells. 3 ml of cells were seeded into medium into each 6 well plate. When one pipette was used up, the cells were mixed in the flask before using them for the next pipette. Compounds for screening were resolved in DMSO, at 1000 fold to the final concentration in the well. The solution was pipetted adding 10 μl solution into 990 μl medium, and the resulting dilution mixed by pipetting.

12 hours after cells were plated, the 400 µl medium was then removed from the cultures and 400 µl of Δ9-THC (T4764-1ML Sigma Aldrich, Merck KGaA; Darmstadt, Germany) or caffeine (C0750-100G, Sigma Aldrich) were added at different concentrations to each well, the final volume of each well is 3 ml. The plate is then incubated for another 48 hours. The supernatant was collected for ELISA assay, and the remaining samples were frozen at −80° C.

ELISA assay was performed on the cells at 0 nM, 0.25 nM, 2.5 nM, 25 nM, 250 nM, or 2500 nM for THC or 0 µM, 0.625 µM, 1.25 µM, 2.5 µM, 5 µM, 10 µM for caffeine. 50 µl of goat anti-PWT1-42 antibody solution was added to the sample and incubated overnight, followed by a 1-hour incubation with 0.1% I-block buffer. The tissue culture supernatant was diluted 1:10 with diluent buffer containing a protease inhibitor. Standards (1000, 500, 250, 125, 62.5, 31.25 pg/ml) were prepared by serial dilution. The plate was washed and 50 µl of sample or standard was added with triplication. 50 µl of both Biosource 40/42 (HS) (primary antibody) Aβ and a standard solution was added to each well and incubated for 3 hours followed by 5× wash with PBST. 100 µl prepared secondary antibody (1:350 anti-rabbit HRP) was added and incubated at 37° C. for 45 minutes on a shaker. The plate was washed; TMB substrate was added (100 µl) and incubated for 10-30 minutes in the dark. The reaction was halted by adding 100 µl stop solution for detection at 450 nm. A 4 parameter regression was used for the standard.

After 6 hours of treatment, THC exhibited a sigmoidal curve, in which the lowest dose of THC 0.25 nM exhibited a minor increase in Aβ levels, which then rapidly decreased with increasing concentrations of THC, as seen in FIG. 1A. THC exhibited markedly drop in Aβ levels compared to caffeine. Analysis showed a significant reduction in Aβ40 levels upon treatment with THC or caffeine versus the control, in a dose-dependent manner, as seen in FIG. 1A.

Figure 1B:
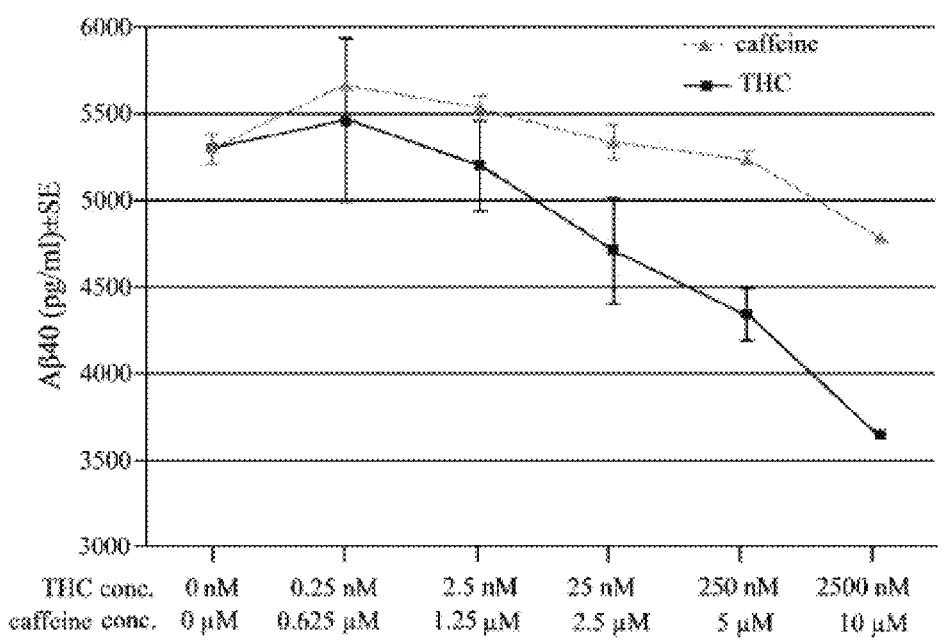
FIG. 1B is a graph of N2a/AβPPswe cells showing Aβ40 (pg/ml) levels in vitro, measured 24 hours from incubation. Cells were either not treated, treated with THC, or treated with caffeine as a positive control. Treatment with THC resulted in a dose-dependent decrease in the production of Aβ40. Data analysis showed $p<0.05$ for 0 nM and 0.25 nM THC versus 2.5 µM THC, and $p>0.05$ for all other groups.

Twenty-four hours after treatment of N2a/AβPPswe cells, Aβ40 concentrations were measured again in the treated cells versus control. An increasing difference in Aβ40 concentrations were noted in both THC treated cells and caffeine treated cells in a dose-dependent manner, as seen in FIG. 1B. Both treatment options THC and caffeine-resulted in an exponential drop in Aβ levels, with THC showing amore efficacy in inhibition.

Figure 1C:
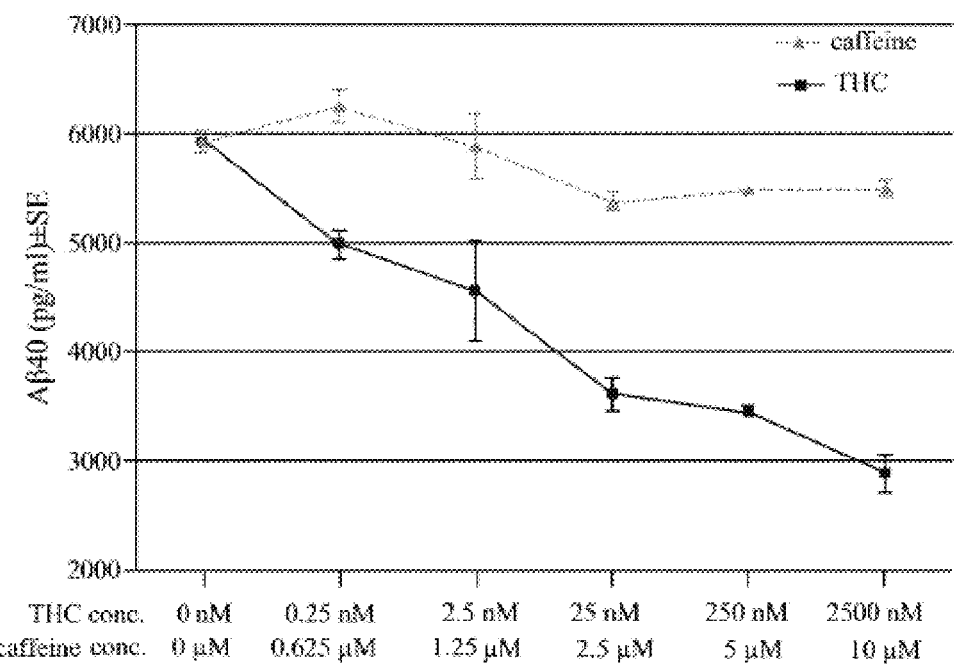
FIG. 1C is a graph of N2a/AβPPswe cells showing Aβ40 (pg/ml) levels in vitro, measured 48 hours from incubation. A dose-dependent decrease in Aβ40 (pg/ml) was observed in THC treated cells. Data analysis showed for THC-treated groups, $p>0.05$ for 0 nM THC versus 0.25 nM THC, and all other groups are $p<0.05$.

The assay was performed again 48 hours after treatment of N2a/AβPPswe cells. THC-treated N2a/AβPPswe cells significantly differed more in Aβ40 concentrations versus the control then at the 6- and 24-hour time point. The significant difference was conserved and greater over each increasing dose of THC and caffeine administered versus the control, as seen in FIG. 1C.

These data show THC can decrease Aβ level in N2a/AβPPswe and suggest THC and caffeine possess inherent anti-Aβ40 properties which are time and dose-dependent. This data also reveals that THC appears to delay or halt the progression of AD by inhibiting the production of Aβ40 peptide in the central nervous system.

The mechanism of action was elucidated for THC's effect on Aβ levels using a sandwich ELISA assay. N2a/AβPPswe cells, as discussed in Example 1, were suspended to $2 \times 10^5$/ml, 3 ml plated into each well, and grown in DMEM with 10% fetal bovine serum, 100 U/mL penicillin, 100 µg/mL streptomycin, and 400 µg/mL G418 (Invitrogen), at 37° C. in the presence of 5% CO2. N2a/AβPPswe cells were subcultured using trypsin, and pipetted numerous times to ensure cells were separated into individual cells. Cells were counted, as provided in Example 1, and proper amount of cell medium and fresh medium was added into new flasks according to the ratio of dilution. Pipetting was performed 10 times to homogenize cells, and 3 ml of cells were seeded into medium into each 6 well plate. When one pipette was used up, the cells were mixed in the flask before using them for the next pipette. Compounds were suspended in DMSO.

12 hours after cells were plated, cells were treated with 25 nM of Δ9-THC (T4764-1ML Sigma Aldrich, Merck KGaA; Darmstadt, Germany), with the known inhibitor of the CB1 receptor, rimonabant, at 0 µM, 100 µM, 10 µM, 1 µM, or 0.1 µM rimonabant. Untreated N2a/AβPPswe cells were used as a control. Treatment was then washed out, i.e. the medium was then removed from the cultures and 3 ml of media containing the treatment compounds were added. Cells were collected at 12 hours afterwards, 48 hours afterwards, 60 hours afterwards, and 72 hours afterwards, and ELISA was conducted on the cells.

ELISA assay was performed on the cells using 50 µl of goat anti-PWT1-42 antibody solution, which was incubated overnight, followed by a 1-hour incubation with 0.1% I-block buffer. The tissue culture supernatant was diluted 1:10 with diluent buffer containing a protease inhibitor. Standards were prepared by serial dilution, as provided in Example 1. The plate was washed and 50 µl of sample or standard was added with triplication. 50 µl of both Biosource 40/42 (HS) (primary antibody) Aβ and a standard solution was added to each well and incubated for 3 hours followed by 5× wash with PBST. 100 µl prepared secondary antibody (1:350 anti-rabbit HRP) was added and incubated at 37° C. for 45 minutes on a shaker. The plate was washed; TMB substrate was added (100 µl) and incubated for 10-30 minutes in the dark. The reaction was halted by adding 100 µl stop solution for detection at 450 nm. A 4 parameter regression was used for the standard.

Figure 2:
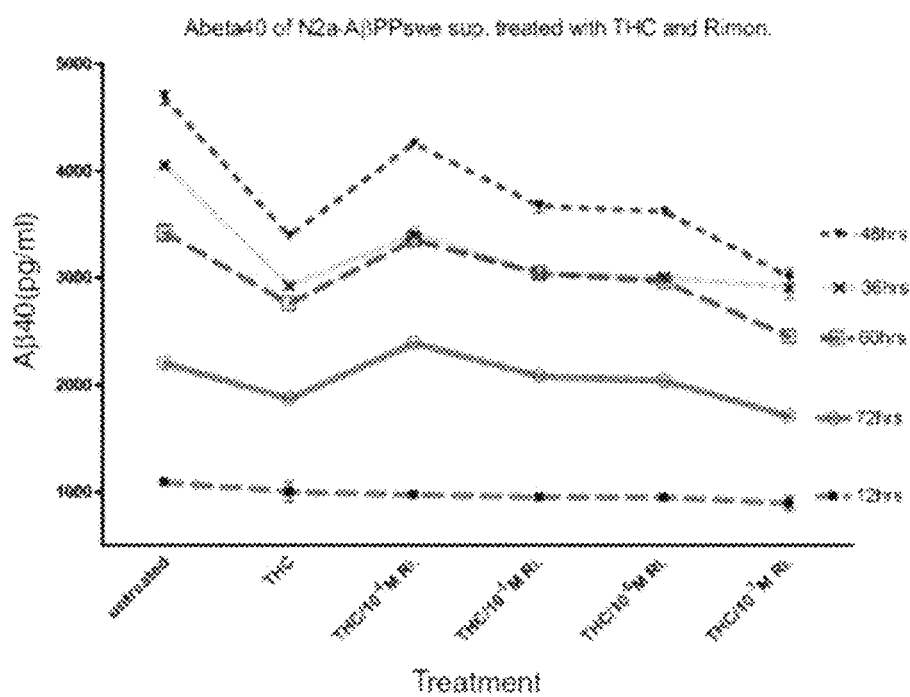
FIG. 2 is a graph showing ELISA assay elucidating a possible mechanism through which THC functions to decrease the synthesis of Aβ in N2a/AβPPswe cells. Aβ level increases at 36 hours and reaches its peak level at 48 hours. Following this mark, it then starts decreasing at 60 hours. The drug treatment benefit time is seen at 36 hours and lasts to 48 hours (the best window time). THC can significantly lower Aβ and this function can be partially blocked by CB1 antagonist Rimon at 10-4 M. However, inhibition function is lost at 10-7 M.

Treatment with THC, i.e. 25 nM THC with no rimonabant, showed marked decreases in Aβ levels at the 36 hour time point, and later time points, as seen in FIG. 2. However, dose-dependent increases in Aβ were observed as the concentration of the inhibitor was increased. A time-dependent effect of the inhibitor was also observed as the assay was repeated at the 12-, 36-, 48-, 60-, and 72-hour mark. Thus, increasing concentrations of inhibitor resulted in the Aβ concentrations increasing, suggesting that THC partially functions through the CB1 receptor to mediate the synthesis of Aβ. The RT-PCR results for CB1 receptor expression level showed that there is no significant upregulation of CB1 receptor when cells were treated with low doses of THC.

A ThT assay was conducted to examine the interaction between THC and Aβ, as ThT incorporates into Aβ when the amyloid protein aggregates, indicating whether there is a direct interaction between THC and Aβ aggregation.

Hexafluoroisopropanol-(HFIP) pretreated Aβ1-40 peptide (Biomer Technology, Pleasanton, Calif.). THC solution was prepared at concentration of 250 nM, 25 nM, 2.5 nM, and 0.25 nM in thioflavin T (ThT) (1.6 µg/ml dissolved in 20 mM Tris-HCL). The THC-ThT was added into black 96 well plates. Unaggregated Aβ peptide solution was thawed, diluted, and immediately added to wells, making the final concentration of Aβ1-40 at 1 µM. Control groups were setup as: 1) aggregation control; 2) control with ThT buffer only; and 3) Tris-HCl buffer only. Plate was mixed and fluorescence was read at 482 nm with excitation 440 nm with Biotek All-in-One plate reader. Fluorescence was screened for 2 hours with 5-minute intervals.

Figure 3A:
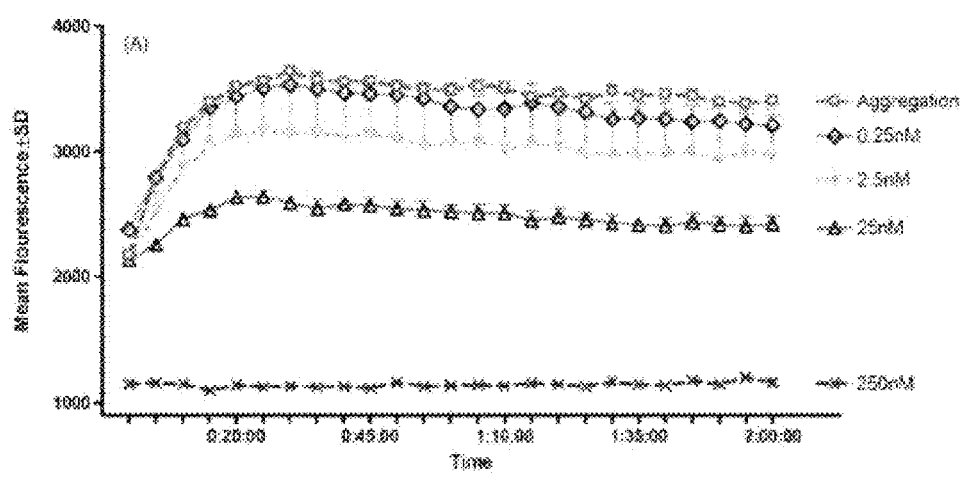
FIG. 3A is a graph showing Aβ aggregation using ThT assay. Fluorescence of Thioflavin T which binds to β-sheet structure of Aβ aggregation was measured. THC treatment at 0.25 nM, 2.5 nM, and 250 nM showed a dose-dependent decrease in the intensity of fluorescence, which indicates that THC directly interferes with the binding of ThT to Aβ peptide resulting in a decrease in Aβ aggregation.
Figure 3B:
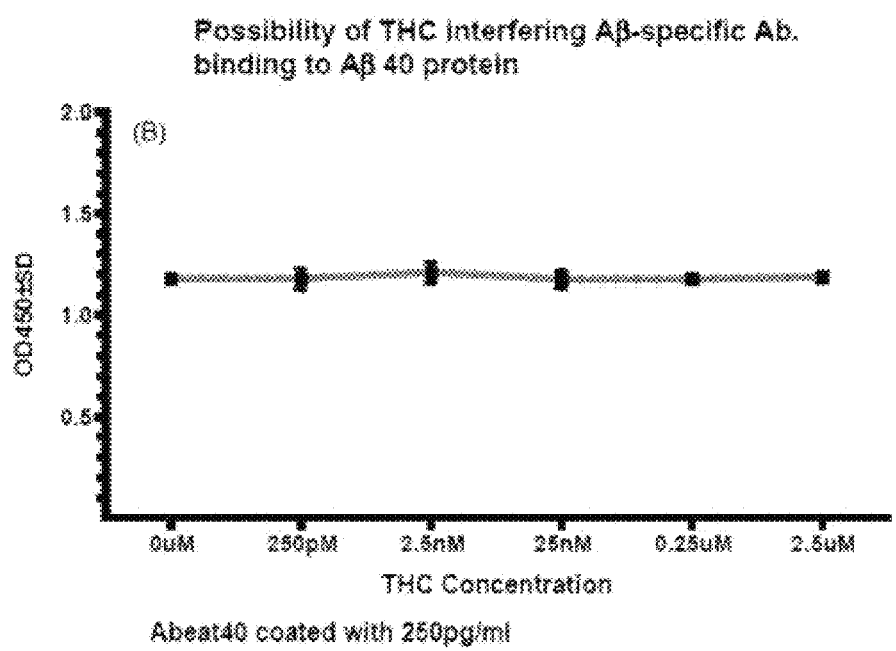
FIG. 3B is a graph showing THC incubated with Aβ peptide to determine the occurrence of THC interference with the major B cell epitope. No identified interference was observed at each increasing concentration of THC.
Figure 4A:
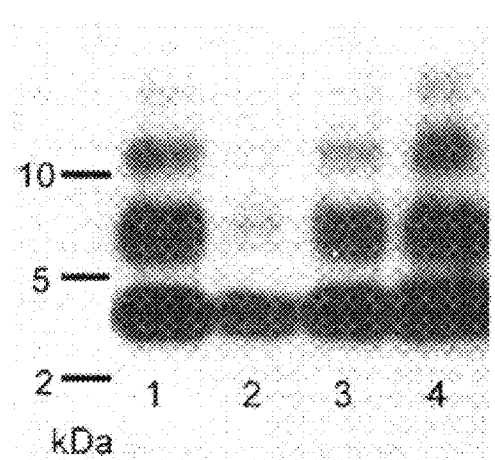
FIG. 4A is a blot showing aggregated Aβ peptide with and without THC treatment. A polyacrylamide gel from a western blot showed aggregated Aβ peptide for an aggregation control, and 100 nM THC, 10 nM THC, and 1 nM THC.
Figure 4B:
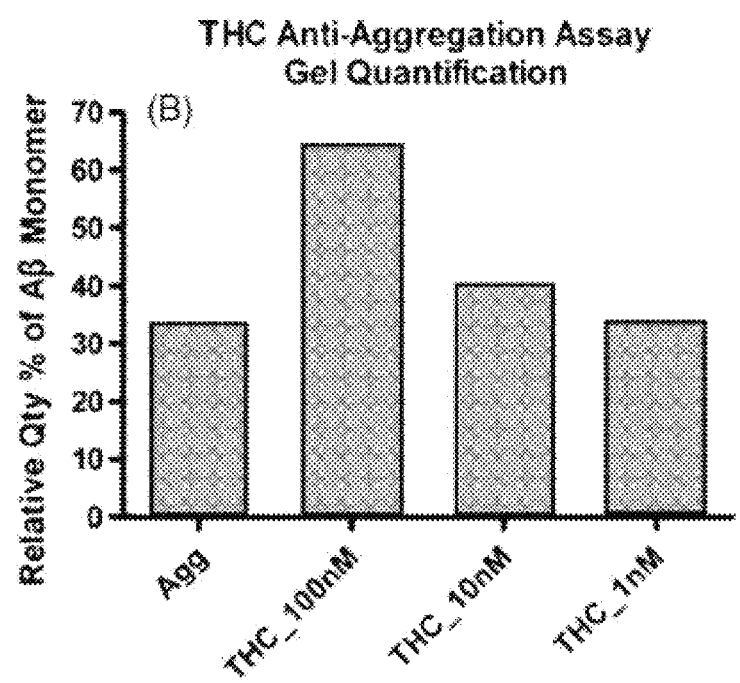
FIG. 4B is a graph showing the relative quantity of Aβ monomer in the anti-aggregation study described in FIG. 4A. Cells were untreated for the aggregation control or treated with and 100 nM THC, 10 nM THC, and 1 nM THC. The data shows that THC increases monomeric Aβ thus decreasing aggregation of Aβ.

In untreated samples, Aβ peptide increased in intensity for the first 20 minutes, followed by a plateauing of fluorescence at around 30 minutes, at which time the intensity remained constant for the duration of the study. When the concentration of THC added to the assay was increased, the intensity of fluorescence in Aβ decreased, evidencing that Aβ peptide directly binds to THC and prevents the uptake of fluorescence, as seen in FIG. 3A. As such, the ThT assay shows THC inhibits Aβ40 aggregation. Moreover, an additional ELISA assay was performed to confirm that the interaction of the Aβ peptide with THC did not shield amino acids 1-10, the major B-cell epitope (Agadjanyan, et al., Prototype Alzheimer's disease vaccine using the immunodominant B cell epitope from beta-amyloid and promiscuous T cell epitope pan HLA DR-binding peptide. J Immunol. 2005; 174: 1580-1586), seen in FIG. 3B. There is no significant difference in absorbance at each concentration of THC, indicating that at each concentration of THC the Aβ antibodies were able to bind with equal distribution and affinity. Therefore, THC's direct interaction with the Aβ peptide will not dampen an immune response to clear the Aβ peptide. Further analysis with western blot was performed measuring the anti-aggregation properties of THC with Aβ peptide. At each increasing concentration of THC, a higher relative % of Aβ monomer was observed correlating with a lower intensity of aggregated Aβ peptide, as seen in FIGS. 4A and 4B. This data shows the direct interaction of THC with Aβ peptide and its ability to bind to the peptide and inhibit aggregation.

Next, the effects of THC on amyloid protein processing were analyzed by testing total GSK-3β and phosphorylated GSK-3β (pGSK-3β) levels. β-actin, a housekeeping gene, was used as a control to indicate that GSK-3β was expressed at a constant rate and that the changes in intensity were not related to the change in expression amount.

The cellular effects of THC were next analyzed. As Aβ processing is mediated by GSK-3β, protein levels were tested. N2a/AβPPswe cells were treated with 2.5 nM or 0.25 nM of THC, as provided in Example 1, and N2a/AβPPswe cell lysate were collected, quantified, and aliquoted.

N2a/AβPPswe cells were cultured as provided above and Δ9-THC added at 0.25 nM and 2.5 nM, as provided in Example 1. After THC treatment for 48 hours, N2a/AβPPswe cell lysate were collected, quantified, and aliquoted. Using 12% Tris-Glycine gel system (Bio-Rad Laboratories, Inc., Hercules, Calif.), protein were separated by electrophoresis and semi-dry transferred to a polyvinylidene difluoride (PVDF) membrane. GSK-3β (Cat #9315, Cell Signaling Technology, Inc. Danvers, Mass.) and β-actin (Cat #A54441, Sigma Aldrich, Merck KGaA; Darmstadt, Germany) antibodies were used as primary antibody. After adding secondary antibody (Goat-anti-Rabbit-HRP Cat #4050-05, Southern Biotech, part of Thermo Fisher Scientific, Waltham, Mass.; Anti-mouse IgG-HRP Cat #A9044, Sigma Aldrich, Merck KGaA; Darmstadt, Germany), the membranes were exposed using ECL substrate (Pierce). After membrane was developed, film with bands were scanned, followed by analysis of gel-quantification software (QuantityOne, from Bio-rad).

Figure 5A:
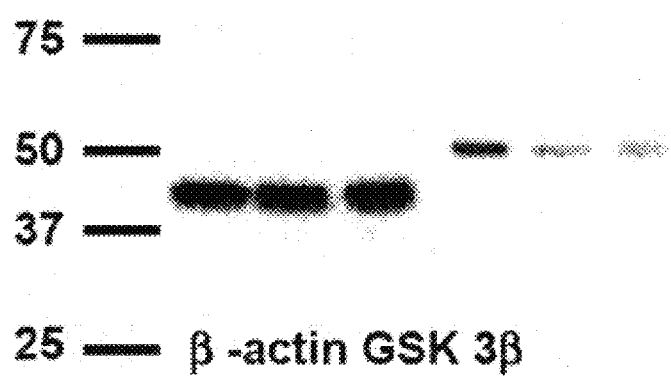
FIG. 5A is a blot showing effects of THC treatment on GSK-3β. A western blot performed to determine the effects of THC on GSK-3β in N2a/AβPPswe. β-actin was used as a control to indicate that the expression rate was constant. The left indicator is molecular weight. Lane 1, 2, and 3 are β-actin level and lane 4, 5, and 6 are GSK-3β expression. 1 and 4 are cell controls (ctrl), 2 and 5 are cells treated with 2.5 nM THC, and lane 3 and 6 are cells treated with 0.25 nM THC.
Figure 5B:
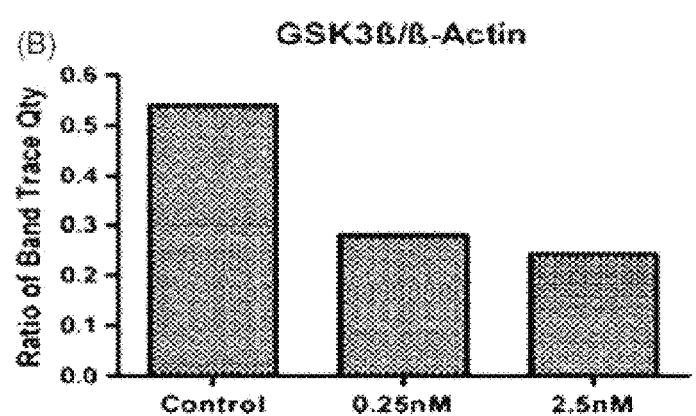
FIG. 5B is a graph showing effects of THC treatment on GSK-3β. GSK-3β expression levels were standardized using β-actin to obtain a value for the ratio of expressed GSK-3β. As shown in the bar graph, THC treatment decreases the expression of GSK-3β.
Figure 5C:
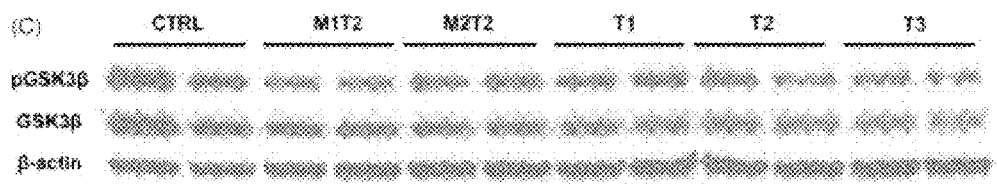
FIG. 5C is a blot showing the effects of treatment of THC on GSK-3β and phosphorylated GSK-3β. Cells were plated in 6 well plate overnight with 25 nM THC, 2.5 nM THC, or 0.25 nM THC added into each designated wells in duplicate. Cells were lysed after 36 hours incubation. Proteins were loaded onto SDS-page gel and then blotted with each antibody after transfer onto PVDF membrane.
Figure 5D:
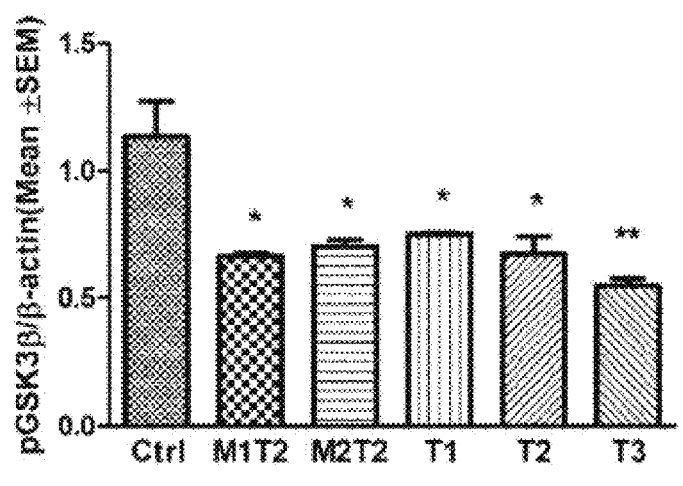
FIG. 5D is a graph showing the effects of treatment on phosphorylated GSK-3β as described in FIG. 5C. Treatment with THC results in a decrease of phosphorylated GSK-3β.

Treatment with even the lowest level of THC from the tests exhibited a sharp decrease in GSK-3 levels in cells, to about half the protein levels seen in the control, and continues to drop with higher concentrations of THC, as shown in FIGS. 5A and 5B. Thus, THC exhibits a dose-dependent decrease in GSK-3β, evidencing that THC is efficacious in modulating and ameliorating the expression of GSK-3β, as well as decreases in neuronal apoptosis by down regulating GSK-3β. Additional studies on N2a/AβPPswe cells treated with 25 nM THC, 2.5 nM THC, or 0.25 nM THC show phosphorylated GSK-3β exhibits similar results, as seen in FIGS. 5C and 5D.

Amyloid processing and ancillary amyloid protein effects were next tested. After stripping the Western, and restaining for AβPP, using anti-Tau (Chuanhai Cao, Tampa, Fla.), anti-pTau (Chuanhai Cao, Tampa, Fla.), and anti-β-actin antibodies (Cat #A54441, Sigma Aldrich, Merck KGaA; Darmstadt, Germany)) were used to detect Tau levels against a protein loading control (β-actin). After data was collected the membrane was stripped using a western blot striping buffer (Cat #21059, Thermo Fisher Scientific, Waltham, Mass.) and stained for AβPP using 6E10 antibody (Cat #803002, BioLegend, Inc., San Diego, Calif.). Anti-mouse secondary horseradish peroxidase (Cat #A9044, Sigma Aldrich, Merck KGaA; Darmstadt, Germany) secondary antibodies were used.

Figure 6A:
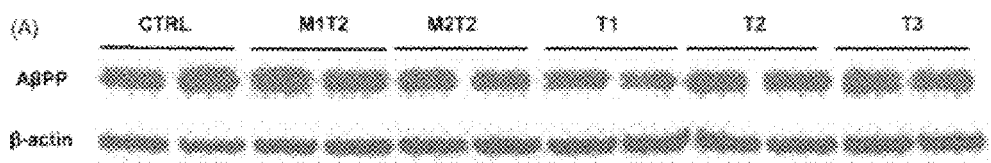
FIG. 6A is a blot showing Aβ processing. AβPP expression was examined in N2a/AβPPswe treated with 25 nM THC, 2.5 nM THC, or 0.25 nM THC using 6E10 anti-Aβ antibody and β-actin as a protein loading control.
Figure 6B:
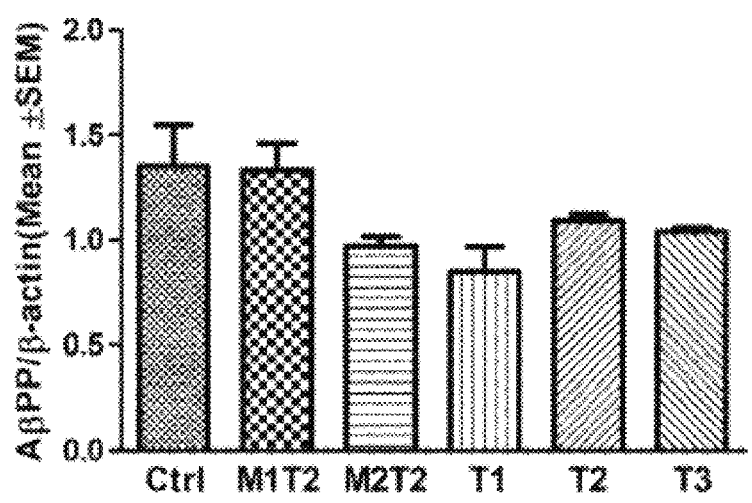
FIG. 6B is a graph showing Aβ processing in N2a/ AβPPswe cells treated with 25 nM THC, 2.5 nM THC, or 0.25 nM THC. Levels of AβPP, standardized to β-actin, expression treated with different drugs were quantified to compare the differences among drug treatment to AβPP level. This data indicates that THC decreases AβPP expression levels.
Figure 6C:
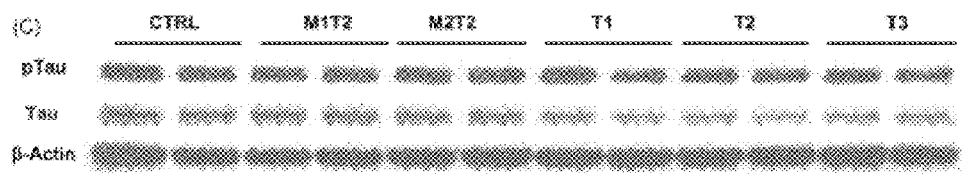
FIG. 6C is a western blot assay showing Tau and phosphorylated Tau levels in N2a/AβPPswe treated with 25 nM THC, 2.5 nM THC, or 0.25 nM THC. Anti-Tau, anti-pTau and β-actin antibodies were used to detect Tau and pTau, and β-actin that served as the protein loading control.
Figure 6D:
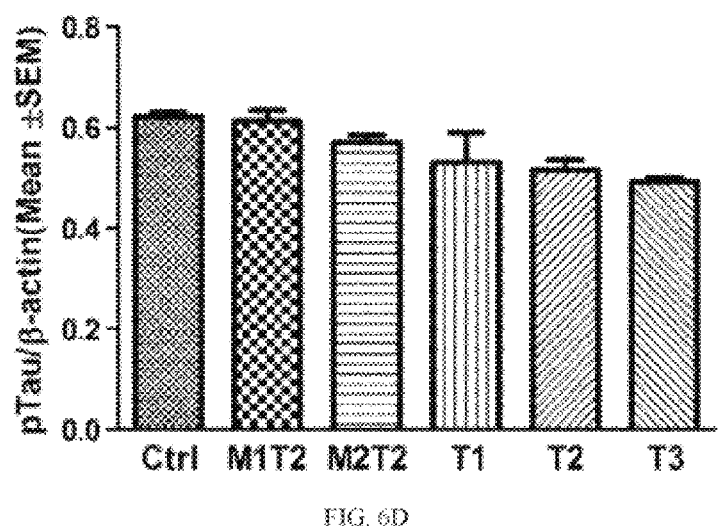
FIG. 6D is a graph showing phosphorylated Tau levels in N2a/AβPPswe cells treated with 25 nM THC, 2.5 nM THC, or 0.25 nM THC. Treatment with THC decreases phosphorylated Tau.
Figure 7:
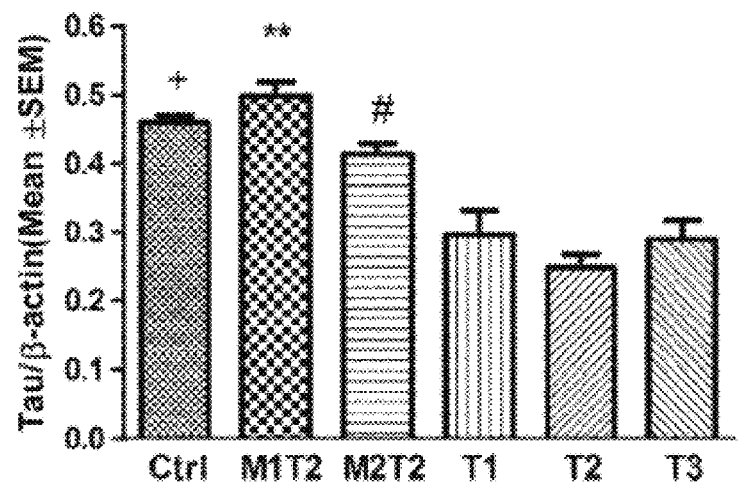
FIG. 7 is a graph showing Tau levels in N2a/AβPPswe cells treated with 25 nM THC, 2.5 nM THC, or 0.25 nM THC. Levels of Tau, standardized to β-actin, expression treated with different drugs were quantified to compare the differences among drug treatment on Tau levels. Treatment with THC reduces the expression of Tau protein. $+p<0.05$ when compared with the THC 25 nM, THC 2.5 nM, and THC 0.25 nM groups. $**p<0.01$ when compared with the THC 25 nM, THC 2.5 nM, and THC 0.25 nM groups. $\#p<0.05$ when compared with THC 2.5 nM group.
Figure 8:
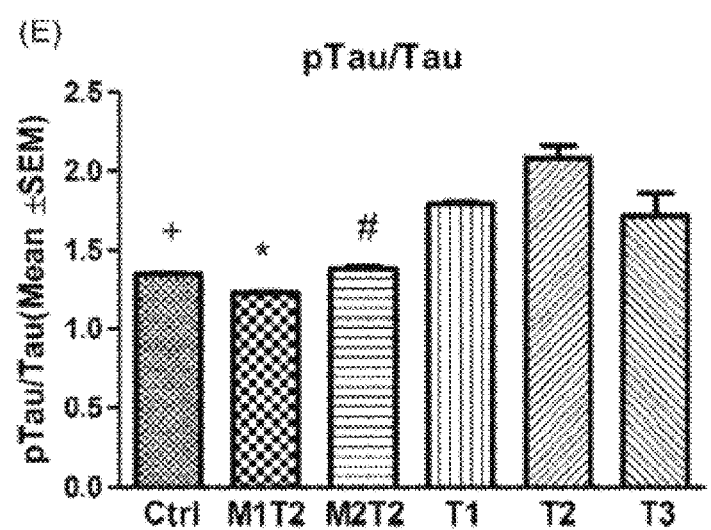
FIG. 8 is a graph showing the ratio of phosphorylated Tau to Tau in N2a/AβPPswe cells treated with 25 nM THC, 2.5 nM THC, or 0.25 nM THC. The data for THC indicates an increase in phosphorylated Tau. $+p<0.05$ when compared with THC 25 nM and THC 0.25 nM groups. $*p<0.01$ when compared with THC 25 nM, THC 2.5 nM, and THC 0.25 nM groups. $\#p<0.05$ when compared with THC 25 nM and THC 2.5 nM groups.

Probing for AβPP showed no significant changes in protein levels, as seen in FIGS. 6A and 6B. After accounting for the background, phosphorylated tau shows a reduction by THC in a dose-dependent manner, as seen in FIGS. 6C and 6D. Interestingly, treatment with 2.5 nM THC showed the lowest level of Tau, as seen in FIGS. 6C and 7, resulting in a peak of pTau:Tau ratio at this concentration, as seen in FIG. 8. Thus, THC can lower pTau expression level with dose-dependent administration, but increase the ratio of pTau/Tau (the activated pTau).

THC was also measured for toxicity versus the caffeine and the untreated N2a/AβPPswe cells, which served as the control, using an MTT assay. Cells were plated in 96-well tissue culture plate at 10,000 cells/well, 100 μl/well. 100 μl THC solution was added at 2× concentrations in each well. Control groups are: 1) cells without THC treatment, cells and fresh medium only and 2) blank, wells with medium without cells. All wells were replicated. Wells were incubated for 36 hours. Cell proliferation kit (Roche 11465007001) was then applied for toxicity assay according to the standard protocol. 10 μl of MTT reagent was first added to each well and incubated at 37° C. for 4 hours. Then 100 μl of solubilization solution was added to each well. These were incubated overnight and optical density (OD) values were read at 575 nm. The percentage of cell viability was calculated as: Cell viability %=(OD−OD blank)/(OD control−OD blank).

Figure 9A:
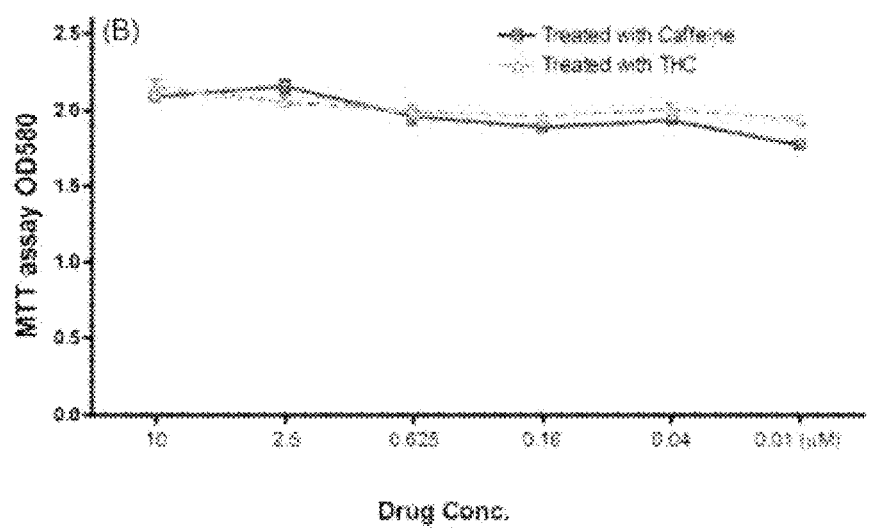
FIG. 9A is a graph showing toxicology studies in THC-treated or caffeine-treated N2a/AβPPswe cells. Data show the reduction of MTT at different concentrations of THC versus the different concentration of caffeine. Untreated N2a/AβPPswe cells were also assayed to compare with the MTT reduction of N2a/AβPPswe cells treated with THC and caffeine at different concentrations. This data shows that there is no toxicity at the different doses of THC.

The MTT assay showed THC-treated cells maintained the same OD levels, indicating no significant difference from the control for toxicity, as seen in FIG. 9A. Further, levels of THC were more consistent than caffeine. The MTT assay confirmed that cells treated at efficacious concentration of THC showed no toxicity, suggesting such a treatment to be safe and effective for further experimentation in the AD animal model. However, valid arguments have transpired in recent times regarding the concern for acute and long-term memory impairment with the use of THC (see, Nakamura, et al., Reversible effects of acute and long-term administration of delta-9-tetrahydrocannabinol (THC) on memory in the rat. Drug Alcohol Depend. 1991; 28: 167-175). It should be clear, however, that the memory impairment observed occurred at concentrations more than a thousand times higher than what is presented here as a beneficial treatment in AD model N2a/AβPPswe cells. The concentrations used in the study are considered to be extremely low, as the concentrations tested were from 2.5 nM of THC down to 0.25 nM of THC. Although some studies with ultra-low doses of THC have indicated neurotoxic roles in rats (Nakamura, et al., Reversible effects of acute and long-term administration of delta-9-tetrahydrocannabinol (THC) on memory in the rat. Drug Alcohol Depend. 1991 August; 28(2): 167-175), newer research shows a neuroprotective role and actually promotes elevation of phosphorylated cAMP response element-binding protein (pCREB) by increasing the levels of brain-derived neurotrophic factor in the frontal cortex (Fishbein, et. al., Long-term behavioral and biochemical effects of an ultra-low dose of 49-tetrahydrocannabinol (THC): neuroprotection and ERK signaling. Exp Brain Res. 2012 September; 221(4):437-48). Furthermore, the dosing used herein is a lower concentration than that in the aforementioned research. Therefore, THC has a therapeutic value, and at low enough doses, the potential benefits strongly prevail over the risks associated with THC and memory impairment. In addition to the Aβ concentration suppression, benefits of THC, analyzed with a western blot and ThT assay, confirmed anti-Aβ aggregate properties by a dose-dependent decrease in fluorescence uptake, and a decrease in intensity of aggregated Aβ in a dose-dependent manner. The positive results suggest possible intermolecular force interactions, preventing the molecular aggregation of Aβ peptides. The conducted ELISA, to ensure the intermolecular interaction of THC with Aβ did not block the major B-cell epitope, showed no interference with antibody binding, which indicated that regardless of the molecular interaction of THC with Aβ, an immune response should not be inhibited.

Studies were conducted on multiple dosings of THC. N2a/AβPPswe cells, as discussed in Example 1, were suspended to $2\times10^5$/ml, 3 ml plated into each well, and grown in DMEM with 10% fetal bovine serum, 100 U/mL penicillin, 100 μg/mL streptomycin, and 400 μg/mL G418 (Invitrogen), at 37° C. in the presence of 5% CO2. N2a/AβPPswe cells were subcultured using trypsin, and pipetted numerous times to ensure cells were separated into individual cells. Cells were counted, as provided in Example 1, and proper amount of cell medium and fresh medium was added into new flasks according to the ratio of dilution. Pipetting was performed 10 times to homogenize cells, and 3 ml of cells were seeded into medium into each 6 well plate. When one pipette was used up, the cells were mixed in the flask before using them for the next pipette. Compounds were suspended in DMSO, as provided in Example 1.

12 hours after plating, cells were treated with various concentrations of Δ9-THC (T4764-1ML Sigma Aldrich, Merck KGaA; Darmstadt, Germany), with untreated N2a/AβPPswe cells used as a control. Multiple dosing regimens were carried out 24 hours after initial treatment. Treatment was then washed out, i.e. the medium was then removed from the cultures and 3 ml of media containing the treatment compounds were added. Cells were collected at 12 hours afterwards last treatment (60 hours post treatment), and ELISA was conducted on the cells.

ELISA assay was performed on the cells using 50 μl of goat anti-PWT1-42 antibody solution, with overnight incubation, and a 1-hour block in 0.1% I-block buffer. The tissue culture supernatant was diluted 1:10 with diluent buffer containing a protease inhibitor. Standards were prepared by serial dilution, as provided in Example 1. The plate was washed and 50 μl of sample or standard was added with triplication. 50 μl of both Biosource 40/42 (HS) (primary antibody) Aβ and a standard solution was added to each well and incubated for 3 hours followed by 5× wash with PBST. 100 μl prepared secondary antibody (1:350 anti-rabbit HRP, Cat #4050-05 Southern Biotech, part of Thermo Fisher Scientific, Waltham, Mass.) was added and incubated at 37° C. for 45 minutes on a shaker. The plate was washed; TMB substrate was added (100 μl) and incubated for 10-30 minutes in the dark. The reaction was halted by adding 100 μl stop solution for detection at 450 nm. A 4 parameter regression was used for the standard.

Figure 9B:
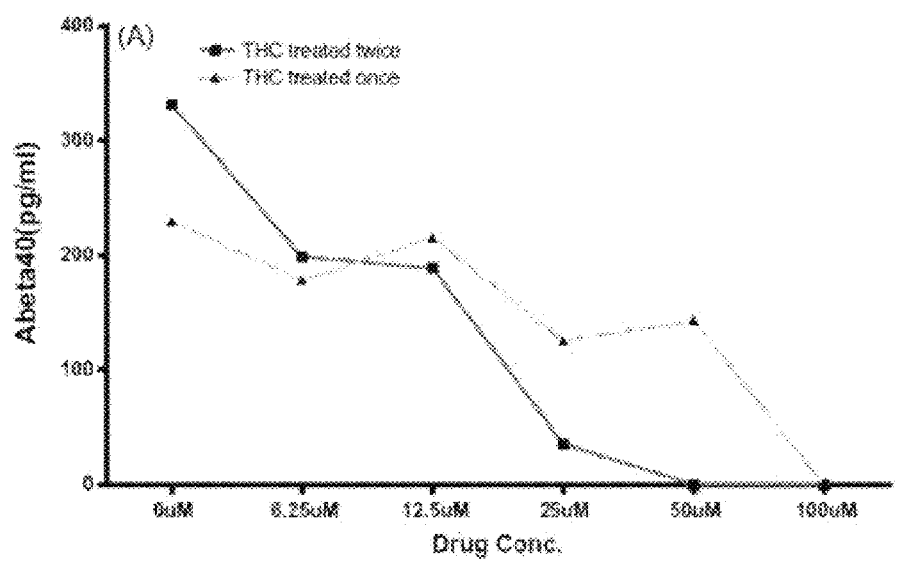
FIG. 9B is a graph showing Aβ40 (pg/ml) concentrations in N2a/AβPPswe cells treated with designated concentrations of THC upon one administration or two administrations delivered 24 hours apart. This data shows that treatments with THC decreases Aβ40.

While treatment of N2a/AβPPswe cells with THC exhibited a drop in Aβ40 levels, as expected from the previous studies, discussed above, multiple dosings, i.e. treating the cells twice with THC 24 hours apart from each treatment, showed a significant decrease in Aβ40 concentration compared to cells treated once from 12 μM and higher concentrations, as seen in FIG. 9B. Further, treatments at 25 μM and greater show significant reductions in Aβ40, suggesting multiple treatments may be efficacious in reducing Aβ40 concentration in N2a/AβPPswe cells and animal models.

The effects of combining THC with other compounds was analyzed using a combination of THC and melatonin. Cells were treated with 2.5 nM of THC and 10 μM or 1 μM melatonin, using the methods discussed above, and N2a/AβPPswe cell lysate collected, quantified, and aliquoted. Using 12% Tris-Glycine gel system (Bio-rad), proteins were separated by electrophoresis and semi-dry transferred to a PVDF membrane. GSK-3β and β-actin antibodies were used as primary antibody. After adding secondary antibody, the membranes were exposed using ECL substrate (Pierce). After membrane was developed, film with bands were scanned, followed by analysis of gel-quantification software (QuantityOne, from Biorad).

Figure 10A:
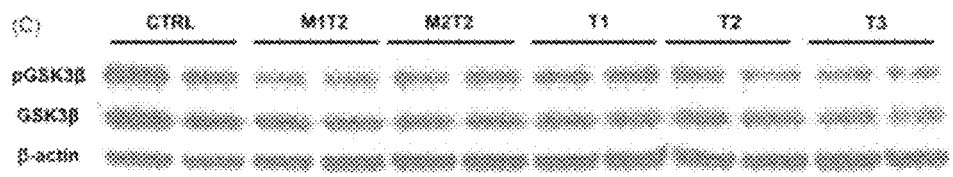
FIG. 10A is a blot showing the effect of THC treatment on GSK-3β and phosphorylated GSK-3β. Cells were plated in 6 well plate overnight and untreated (CTRL, control), or 10-5 M Melatonin with 2.5 nM THC, 10-6 M Melatonin with 2.5 nM THC; THC, 25 nM THC 2.5 nM THC, 0.25 nM THC added into each designated well in duplicate. Cells were lysed after 36 hours incubation. Proteins were loaded onto SDS-page gel and then blotted with each antibody after transfer onto PVDF membrane.
Figure 10B:
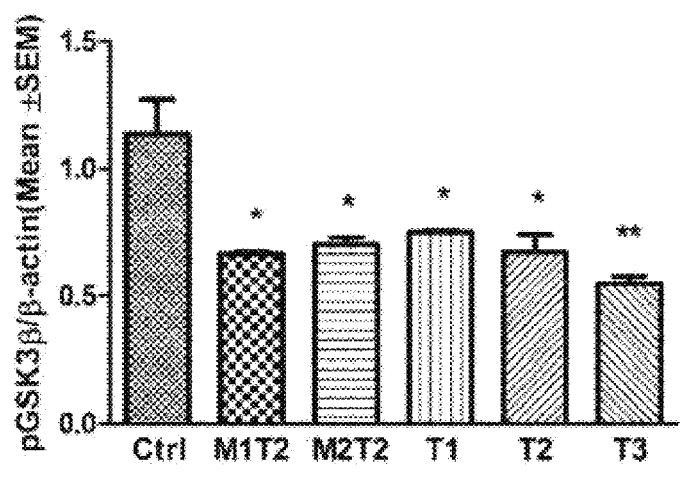
FIG. 10B is a graph showing the effects of treatment on phosphorylated GSK-3β as set out in FIG. 10A. The data shows that treatment with THC or THC in combination with melatonin decreases phosphorylated GSK-3β. One-way ANOVA was applied to the data. $p<0.05$ when compared with control group. $**p<0.01$ when compared with control group.

The western blot assay performed to examine the effect of the combination treatment of THC and melatonin show reductions in GSK-3β at 2.5 nM THC and both concentrations of melatonin, as seen in FIG. 10A. Further, reductions in phosphorylated GSK-3β are equivalent to reduced protein levels upon treatment with THC alone, as seen in FIG. 10B. This suggests that the combination of THC and melatonin is as efficacious in modulating and ameliorating GSK-3β expression as THC, and could decrease neuronal apoptosis by down regulating GSK-3β.

Figure 11A:
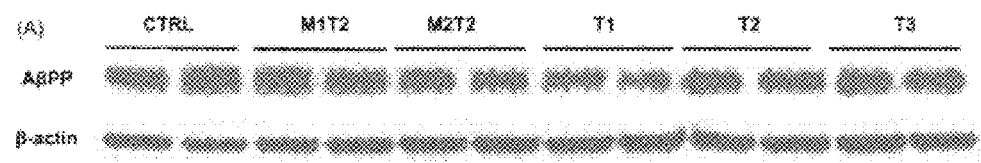
FIG. 11A is a blot showing Aβ processing. AβPP expression was examined in N2a/AβPPswe treated as follows: untreated (CTRL, control), or 10-5 M Melatonin with 2.5 nM THC, 10-6 M Melatonin with 2.5 nM THC; using 6E10 anti-Aβ antibody and β-actin as a protein loading control.
Figure 11B:
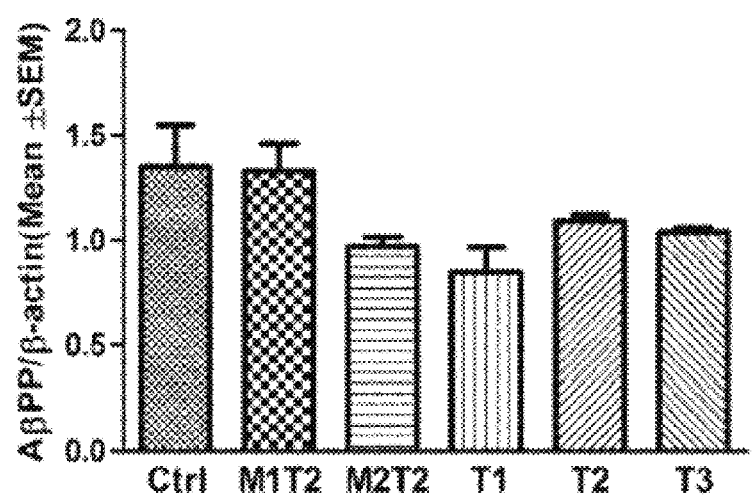
FIG. 11B is a graph based on the western blot study set out in FIG. 11A showing Aβ processing in N2a/AβPPswe cells treated as follows: untreated (CTRL, control), or 10-5 M Melatonin with 2.5 nM THC, 10-6 M Melatonin with 2.5 nM THC. Levels of AβPP, standardized to β-actin, expression treated with different drugs were quantified to compare the differences among drug treatment to AβPP level. The data shows that certain combinations of THC and melatonin (M1T2) do not change AβPP expression levels, as contrasted with THC alone (T1, T2, T3), which decreases AβPP expression levels
Figure 11C:
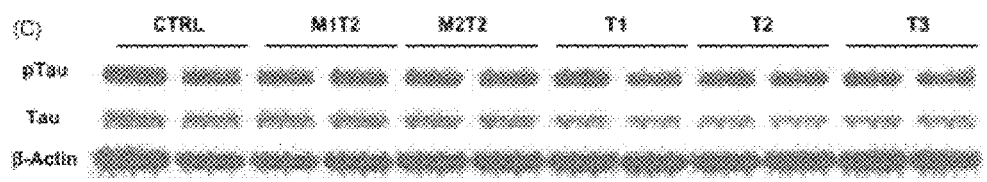
FIG. 11C is a western blot assay showing Tau and phosphorylated Tau levels in N2a/AβPPswe treated as follows: untreated (CTRL, control), or 10-5 M Melatonin with 2.5 nM THC, 10-6 M Melatonin with 2.5 nM THC. Anti-Tau and anti-pTau antibodies were used to detect AβPP and β-actin that served as the protein loading control.
Figure 11D:
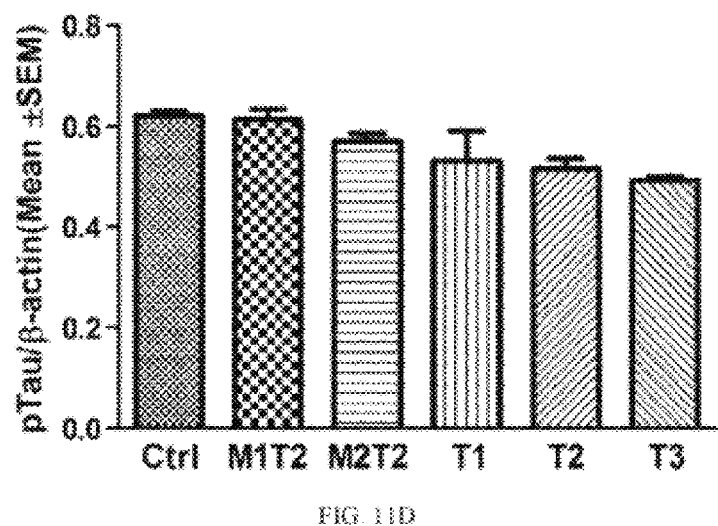
FIG. 11D is a graph based on the study outlined in FIG. 11C, showing phosphorylated Tau levels in N2a/AβPPswe cells treated as follows: untreated (CTRL, control), or 10-5 M Melatonin with 2.5 nM THC, 10-6 M Melatonin with 2.5 nM THC. The combination of THC and melatonin either maintains (M1T2) or decreases (M2T2) phosphorylated Tau.
Figure 12:
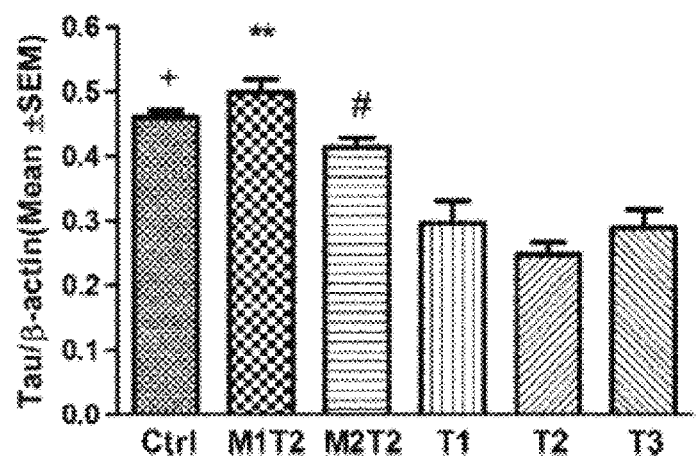
FIG. 12 is a graph showing Tau levels in N2a/AβPPswe cells treated as follows: untreated (CTRL, control), or 10-5 M Melatonin with 2.5 nM THC, 10-6 M Melatonin with 2.5 nM THC. Levels of Tau, standardized to β-actin, expression treated with different drugs were quantified to compare the differences among drug treatment on Tau levels. The data shows that at certain ratios of THC to melatonin (M2T2) Tau expression is decreased.
Figure 13:
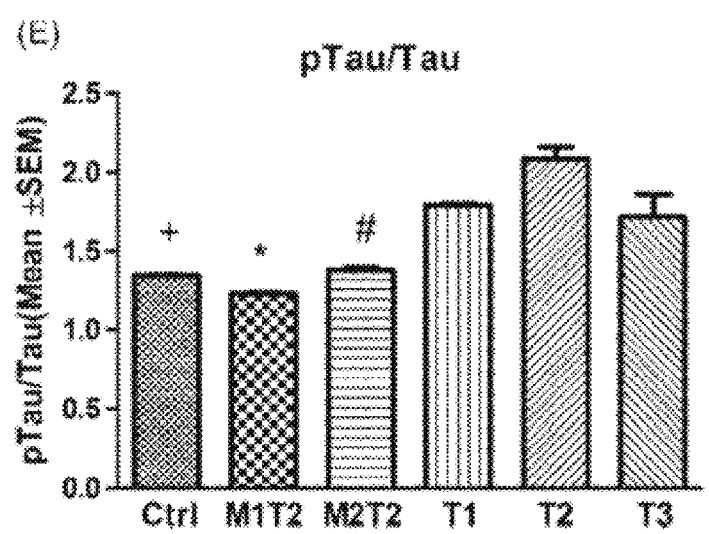
FIG. 13 is a graph showing the ratio of phosphorylated Tau to Tau in N2a/AβPPswe cells treated as follows; untreated (CTRL, control), or 10-5 M Melatonin with 2.5 nM THC, 10-6 M Melatonin with 2.5 nM THC. The data shows that certain ratios of THC and melatonin (M1T2, M2T2) decrease phosphorylated Tau, as contrasted with THC alone (T1, T2, T3) that increases phosphorylated Tau.

Amyloid processing and ancillary amyloid protein effects were next tested, using the methods described in Example 2. Staining with 6E10 antibody showed AβPP levels were not affected by treatment of THC and melatonin at higher melatonin concentrations, i.e. at 2.5 nM THC and 10 μM melatonin, but did decrease to levels consistent with THC-only treatments at lower concentrations of 2.5 nM THC and 1 μM melatonin, as seen in FIGS. 11A and 11B. Both Tau and pTau expression levels did not appear affected by combination treatment of THC and melatonin, at either concentration, as seen in FIG. 11C. Further, quantification of pTau, and Tau after accounting for background, showed an effect upon treatment, as seen in FIG. 11D, and FIG. 12. Accordingly, the ratio of pTau:Tau, as seen in FIG. 13, was not significantly altered in combined treatment, whereas THC-only treatment did reduce Tau levels.

Figure 14A:
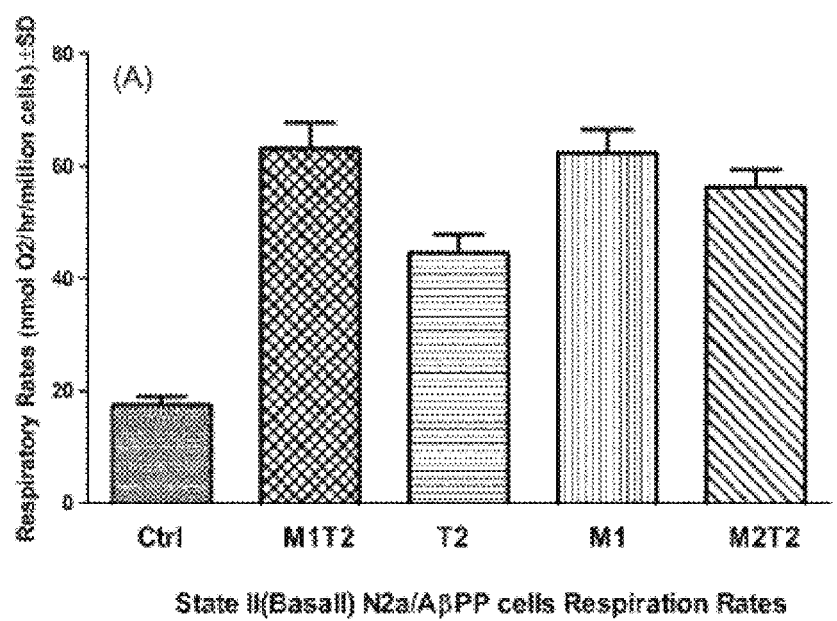
FIG. 14A is a graph showing basal mitochondrial function after treatment with THC and a combination of THC and melatonin. N2a/AβPPswe cells were cultured in 10 cm tissue culture plate and then treated with drugs for 36 hours and mitochondria were harvested and tested for their ability of using oxygen utilization. Samples were loaded as follows; Ctrl, Control, or 10-5 M Melatonin with 2.5 nM THC, 10-6 M Melatonin with 2.5 nM THC, 2.5 nM THC, 10-5 M Melatonin, or 10-6 M Melatonin+2.5 nM THC. The data shows that THC alone (T2), as well as the combination of THC and melatonin (M1T2, M2T2) enhance mitochondrial function.
Figure 14B:
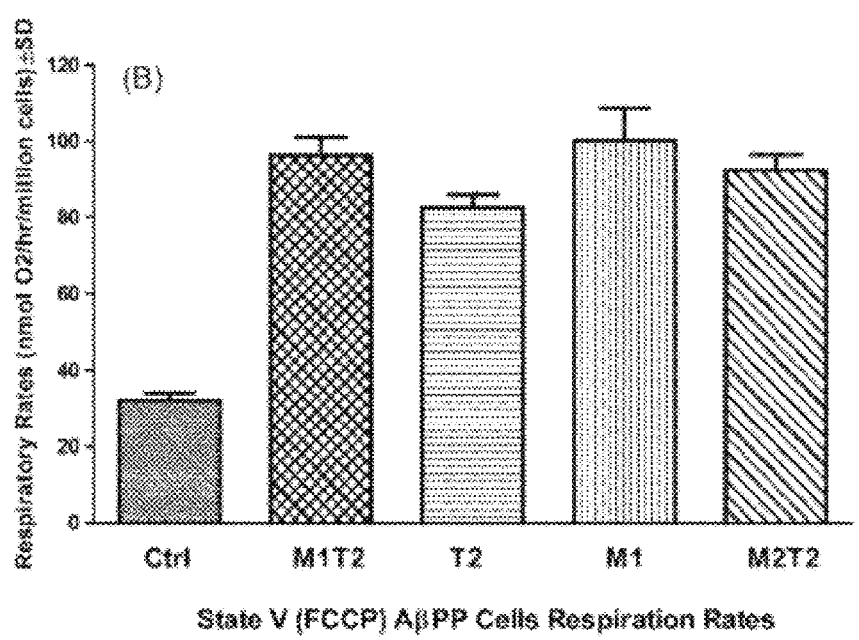
FIG. 14B is a graph showing mitochondrial function in the presence of FCCP after treatment with THC alone as well as with a combination of THC and melatonin. N2a/AβPPswe cells were cultured in 10 cm tissue culture plate and then treated with drugs for 36 hours and mitochondria were harvested and tested for their ability of using oxygen utilization. Samples were loaded as follows; Ctrl, Control, or 10-5 M Melatonin with 2.5 nM THC, 10-6 M Melatonin with 2.5 nM THC, 2.5 nM THC, 10-5 M Melatonin, or 10-6 M Melatonin+2.5 nM THC. The data shows that THC (T2) alone as well as the combination of THC and melatonin (M1T2, M2T2), enhance mitochondrial function.

The respiratory function of isolated mitochondria was measured using a miniature Clark type oxygen electrode (Strathkelvin Instruments, MT200A chamber, Glasgow, UK) using methods published in Dragicevic et al. (Dragicevic, et al., Melatonin treatment restores mitochondrial function in Alzheimer's mice: a mitochondrial protective role of melatonin membrane receptor signaling. J Pineal Res. 2011; 51: 75-86). Treatment of N2a/AβPPswe cells showed THC enhances mitochondrial function, as isolated mitochondria from N2a/AβPPswe cells showed higher oxygen utilization when treated with 2.5 nM THC at early stages of respiration, seen in FIG. 14A, as well at late stages, as seen in FIG. 14B. Combined treatment of THC with 10 μM or 1 μM melatonin showed a slight elevation in respiration compared to THC-only treatment, and was comparable to 10

μM melatonin, seen in FIGS. 14A and 14B. This indicated that THC does not interfere with melatonin's enhancement of the mitochondria.

Therapeutic doses of Δ9-tetrahydrocannabinol (THC) were tested to determine the efficacy of the compounds with respect to slowing or halting the hallmark characteristics of Alzheimer's disease. N2a-variant amyloid-β protein precursor (AβPP) cells were incubated with THC and assayed for amyloid-β (Aβ) levels from 6- to 48-hours after THC administration. The studies showed contacting a cell with tetrahydrocannabinol at extremely low concentrations, reducing amyloid-β protein synthesis. This methodology is useful for treating a patient having Alzheimer's disease, through administration of THC, to the patient. Nonlimiting examples of THC include dronabinol and Δ9-THC. Where the composition is used for Alzheimer's disease treatment, THC is administered to reach a concentration in the cerebrospinal fluid of between 0.25 nM and 250 nM.

The tetrahydrocannabinol is provided to a cell at levels sufficient to achieve a concentration of between 0.25 nM and 250 nM at the cell.

Calculating Human Dose Amounts: The conversion of in vitro cellular drug concentration to human equivalent drug dose is established methodology. (See: http://www.protocol-online.org/biology-forums/posts/30561.html; https://www-.tocris.com/resources/molarity-calculator).

Human equivalent doses are converted from cellular doses using a standard formula that uses molecular weight, average blood volume of an adult human, and cellular concentration. Mass (g)=Concentration (mol/L) multiplied by Volume (L) multiplied by Molecular Weight (g/mol). This formula assumes that drug is 100% bioavailable. Most drugs are not 100% bioavailable. For example, THC's bioavailability is 30% (McGilveray I J, Pain Res Manag. 2005 Autumn; 10 Suppl A:15A-22A). The bioavailability of melatonin is 15%. (DeMuro et al, J Clin Pharmacol. 2000 July; 40(7):781-4). Thus, the above formula has to be modified to account for bioavailability.

Conversion of THC and melatonin from cellular dose to human equivalent dose: The ultra-low doses of THC used in the study is in the range of 2.5 nM to 250 nM at the cellular level. This converts to a human dose in the range of 3.93 micrograms/kg to 393 micrograms/kg, assuming 5,000 ml of human blood volume, 100% bioavailability, and a molecular weight of 314.46 g/mol. The conversion from cellular dose to human dose considering 30% bioavailability is shown in Table 1. Similarly, the conversion of melatonin from cellular dose to human dose accounting for 15% bioavailability is shown in Table 1.

Mass (g)=Concentration (mol/L)×Volume (L)×Molecular Weight (g/mol)

THC Dose:

Mass (g)/0.3 (bioavailability correction)=Human equivalent dose for THC 3.9308/0.3=13.102 micrograms/70 kg body weight Per Kg body weight=0.187 micrograms or 0.00018 mg/Kg body weight Melatonin Dose:

Mass (g)/0.15 (bioavailability correction)=Human equivalent dose for melatonin 1.1613/0.15=7.73 mg/70 kg body weight Per Kg body weight=7.73/70=0.11 mg/Kg

TABLE 1

|  |  | THC | Melatonin |
| --- | --- | --- | --- |
| Avg. blood volume | 5,000 ml |  |  |
| Molecular weight |  | 314.46 g/mol | 232.278 g/mol |
| Bio-availability |  | 30% | 15% |
| Cellular concentration (concentration at targeted cell) |  | 2.5 nM-250 nM | 1 μM-10 μM |
| Human dose/kg (dose necessary to achieve cellular concentration above) |  | 0.2 μg/kg-.02 mg/kg | 0.11 mg/kg-1.1 mg/kg |
| Human dose (example) | 70 kg human Patient dose | 13.1 μg-1.3 mg | 7.7 mg-77.3 mg |
| FDA recommended human dose per day* |  | 5 mg-20 mg | 3 mg-10 mg |
| FDA dose/kg body weight |  | 0.07 mg/kg to 0.28 mg/kg |  |

*FDA reference: FDA labeling for Marinol (500012 Rev Sep. 2004)

Multiple THC treatments were found to increase efficacy of the composition, indicating multiple treatments are beneficial. Dosing is provided or administered 24 hours apart (FIG. 6A) The THC is administered at levels or doses to achieve a concentration of between 0.25 nM and 250 nM at the cell, as provided above.

In certain variations of the invention, the cell is contacted with melatonin along with THC. Melatonin is provided to reach a concentration of between 1 μM and 10 μM. Where the composition is administered to a patient, the dose is provided to reach a concentration in the cerebrospinal fluid of between 1 μM and 10 μM. The melatonin is optionally administered at doses to obtain reach a concentration in the cerebrospinal fluid of between 1 μM and 10 μM. Optionally, melatonin is provided at about 0.01 mg/kg to about 0.18 mg/kg.

In specific variations of the invention, melatonin is provided at about 0.11 mg/kg-1.1 mg/kg, the methods provided above are also useful in reducing amyloid-β protein phosphorylation, as well as reducing amyloid protein processing. Thioflavin T assays and western blots confirm THC possesses direct anti-Aβ aggregation properties, directly interacting with Aβ peptide to inhibiting aggregation. It also alters glycogen synthase kinase-3β (GSK-3β) and related signaling pathways to reduce amyloidogenic protein processing.

A method is also disclosed for treating Alzheimer's disease by administering a therapeutically effective amount of a composition a patient suffering from Alzheimer's disease. The composition contains THC and melatonin. Low doses of THC enhance mitochondria function and do not inhibit melatonin's enhancement of mitochondria function. This supports the use of THC with melatonin as a therapeutic treatment option for Alzheimer's disease. The composition is optionally administered orally, intravenously, intraarterially, intranasal and via inhalation. The composition is administered at a dose to achieve a concentration of THC in the cerebrospinal fluid of between 0.25 nM and 250 nM and a concentration of melatonin in the cerebrospinal fluid of 0.25 nM, 1 nM, or 2.5 nM.

A composition of THC and melatonin is also contemplated, as discussed above.

The pharmaceutical compositions of the subject invention can be formulated according to known methods for preparing pharmaceutically useful compositions. Furthermore, as used herein, the phrase "pharmaceutically acceptable carrier" means any of the standard pharmaceutically acceptable carriers. The pharmaceutically acceptable carrier can include diluents, adjuvants, and vehicles, as well as implant carriers, and inert, non-toxic solid or liquid fillers, diluents, or encapsulating material that does not react with the active ingredients of the invention. Examples include, but are not limited to, phosphate buffered saline, physiological saline, water, and emulsions, such as oil/water emulsions. The carrier can be a solvent or dispersing medium containing, for example, ethanol, polyol (for example, glycerol, propylene glycol, liquid polyethylene glycol, and the like), suitable mixtures thereof, and vegetable oils. Formulations are described in a number of sources that are well known and readily available to those skilled in the art. For example, Remington's Pharmaceutical Sciences (Martin E W [1995] Easton Pa., Mack Publishing Company, 19th ed.) describes formulations which can be used in connection with the subject invention.

All data generated herein was analyzed with one-way ANOVA and post hoc analysis conducted with Turkey's group analysis. A value for $p<0.05$ was considered as statistical significance (GraphPad 6.0). All graphs were graphed with GraphPad 6.0 software.

Advances in therapeutics to prevent AD, or delay the progression, are currently being made. Recent research has shown caffeine and coffee are effective in limiting cognitive impairment and AD pathology in the transgenic mouse model by lowering brain Aβ levels, which are thought to be central to the pathogenesis of AD (Arendash & Cao, Caffeine and coffee as therapeutics against Alzheimer's disease. J Alzheimers Dis. 2010; 20 (Suppl 1): S117-S126). Similarly, the current study shows the in vitro anti-Aβ activity of caffeine, and of another naturally occurring compound, THC.

N2a/AβPPswe cells were incubated separately with various concentrations of caffeine, melatonin, and THC. The relative anti-Aβ effect of THC was observed to increase in a time-dependent manner. A dose-dependent decrease in Aβ concentration was noticed at lower concentrations of THC, as compared to caffeine. Further evidence shows that N2a/AβPPswe cells, treated twice with THC, show an even greater reduction in Aβ levels at slightly higher concentrations. Although it might have been predicted that caffeine and THC may function in a synergistic effect to reduce the Aβ load in N2a/AβPPswe cells, no synergy was observed.

Example 1: The Effect of THC on Aβ40 and AβPP Expression, and the Effect of the Combination of THC and Melatonin on AβPP Expression in N2a/AbPswe Cells Studies prior to 2015 reveal that THC and melatonin reduce the secretion of APP and Aβ expression levels. We set out some of the studies prior to 2015 and one study in 2015 to support the statement that THC and melatonin reduce the secretion of APP and Aβ expression levels. For example:

A 1997 study on PC12 cells showed that melatonin reduced the secretion of soluble APP. (Song and Lahari, Melatonin alters the metabolism of the beta-amyloid precursor protein in the neuroendocrine cell line PC12. J Molecular Neuroscience 1997: 75-92.

A 1998 study PC12 cells showed that melatonin prevents Aβ aggregation. (Pappolia M, Inhibition of Alzheimer's beta fibrillogenesis by melatonin, Jour. Of Biological Chemistry 1998: 7185-8).

A 2001 study on neuroblastoma cells showed that administration of melatonin resulted in a reduction of Aβ levels. (Olivieri, et al. Melatonin protects SHSY5Y neuroblastoma cells from cobalt-induced oxidative stress, neurotoxicity and increased beta-amyloid secretion. J Pineal Res. 2001: 320-325).

A 2001 study on neuronal cells showed that melatonin reduced Aβ aggregation. (Poeggeler B, Melatonin Reverses the Profibrillogenic Activity of Apolipoprotein E4 on the Alzheimer Amyloid Aβ Peptide. Biochemistry. 2001 Dec. 11; 40(49):14995-5001.)

A 2003 study on a transgenic model of AD showed a reduction in Aβ levels with no change in APP levels. (Matsubara, Melatonin increases survival and inhibits oxidative and amyloid pathology in a transgenic model of Alzheimer's disease. J Neurochem. 2003 June; 85(5):1101-8.)

In 2004 a study on transgenic mice showed that melatonin reduces Aβ levels in the frontal cortex. (Feng, Melatonin alleviates behavioral deficits associated with apoptosis and cholinergic system dysfunction in the APP 695 transgenic mouse model of Alzheimer's disease. J Pineal Res. 2004 September; 37(2): 129-36)

A 2008 study on N2A cells found that melatonin reduced Aβ levels. (Wang, Effect of melatonin and melatonylvalpromide on beta-amyloid and neurofilaments in N2a cells. Neurochem Res. 2008 June; 33(6):1138-44.)

A 2009 study on a transgenic mice model of AD showed that in the entorhinal cortex and hippocampus, melatonin decreased the aggregation of Aβ, while the soluble oligomeric forms of Aβ1-40 and Aβ1-42 were unchanged. (Olcese J M and Cao, Protection against cognitive deficits and markers of neurodegeneration by long-term oral administration of melatonin in a transgenic model of Alzheimer disease. J Pineal Res. 2009 August; 47(1):82-96.)

In 2010 a study conducted on rats showed that melatonin reduced hippocampal generation. (Ng et al, Melatonin reduces hippocampal beta-amyloid generation in rats exposed to chronic intermittent hypoxia. Brain Res. 2010 Oct. 1; 1354:163-71.)

A study in 2012 on 3xTg-Ad mice showed that melatonin decreased soluble Aβ oligomers in the brain. (Garcia-Mesa, Melatonin plus physical exercise are highly neuroprotective in the 3xTg-AD mouse. Neurobiol Aging. 2012 June; 33(6): 1124.e13-29.)

A study in 2015 conducted on a rat model of sporadic AD showed that melatonin attenuates Aβ accumulation. (Rudnitskaya, Melatonin Attenuates Memory Impairment, Amyloid-β Accumulation, and Neurodegeneration in a Rat Model of Sporadic Alzheimer's Disease. J Alzheimers Dis. 2015; 47(1):103-16.)

Another study done in 2015 on transgenic mice showed that melatonin decreased Aβ1-41 levels. (O'Neal-Moffitt, Prophylactic melatonin significantly reduces Alzheimer's neuropathology and associated cognitive deficits independent of antioxidant pathways in AβPPswe/PS1 mice. Mol Neurodegener. 2015 Jul. 11; 10:27.

Melatonin decreases AβPP expression and Aβ production. (Song and Lahari, Melatonin alters the metabolism of the Beta-amyloid precursor protein in the neuroendocrine cell line PC12. J Molecular Neuroscience 1997: 75-92) (Matsubara et al. Melatonin increases survival and inhibits oxidative and amyloid pathology in a transgenic model of AD. J Neurochem. 2003 June 85(5): 1101-8)

From the foregoing literature, it could be expected that the combination of THC and melatonin would decrease AβPP expression. However, as seen in FIG. 6A and FIG. 6B, it has been found that the combination of ultra-low THC with melatonin (M1T2 for example) does not decrease the APP protein expression level. This is important as maintaining APP protein levels is critical for the normal functioning of neurons.

APP is a transmembrane protein that consists of larger external cellular N-terminal end, a transmembrane domain and short C-terminal cytoplasmic domain. Several studies have demonstrated that APP is required for the synaptic formation neuronal survival and neural outgrowth (Priller C, Bauer T, Mitteregger G, Krebs B, Kretzschmar H A, Herms J (July 2006). "Synapse formation and function is modulated by the amyloid precursor protein". The Journal of neuroscience. 26 (27): 7212-21; Roch J M1, Masliah E, Roch-Levecq A C, Sundsmo M P, Otero D A, Veinbergs I, Saitoh T. Increase of synaptic density and memory retention by a peptide representing the trophic domain of the amyloid beta/A4 protein precursor. Proc Natl Acad Sci USA. 1994 Aug. 2; 91(16):7450-4; Randall A D, Witton J, Booth C, Hynes-Allen A, Brown J T. The functional neurophysiology of the amyloid precursor protein (APP) processing pathway. Neuropharmacology. 2010 September-October; 59(4-5): 243-67). The most recent study has indicated that APP is a neuroprotective factor.

As APP plays a critical role in the health and functioning of neurons, it is imperative that APP levels be kept normal. Therefore, our ultra-low dose of THC in combination with melatonin can help maintain the balance and keep the down regulation of APP in check. The offers advantages over THC or melatonin monotherapy that has been shown to disrupt the homeostasis of APP and lead to a deterioration of normal functioning neurons.

It is thus unexpected that an ultra-low dose of THC and melatonin does not decrease AβPP production as THC alone does.

Example 2: The Effect of THC and the Effect of the Combination of THC and Melatonin on Mitochondrial Function in N2a/AβPPswe Cells Our findings show an un-expected result, at ultra-low doses THC works differently from a high dosage of THC, including at the levels recommended by the FDA for Dronabinol. At ultra-low doses THC enhances mitochondrial function, rather than diminishing mitochondrial function. As explained before, the recommended FDA adult human dose for Dronabinol is between 5 milligrams to 20 milligrams. The highest dose of THC considered in our study is almost 4 times lower than the lowest FDA recommended dose.

Several studies have shown that high dose of THC decreases mitochondrial function whereas we show that ultra-low-dose of THC enhances mitochondrial function (FIG. 14A and FIG. 14 B). Examples of early studies that show that cannabinoids can decrease oxidative metabolism of isolated mitochondria. The influence of delta9-tetrahydrocannabinol, cannabinol and cannabidiol on tissue oxygen consumption). THC at a concentration of 10 to 50 micromolar affect the mitochondrial function and act as an inhibitor of mitochondrial function and induce cell death. (Cannabinoid receptor agonists are mitochondrial inhibitors: a unified hypothesis of how cannabinoids modulate mitochondrial function and induce cell death. Athanasiou et al., Biochem Biophys Res Commun. 2007 Dec. 7; 364(1):131-7). In the year 2000, Costa and Colleni demonstrated that repeated high doses of THC (10 mg/Kg body weight) dampen the brain energy metabolism in rat brains. (Barbara Costa and Mariapia Colleoni; Changes in rat brain energetic metabolism after exposure to anandamide or $\Delta^9$-tetrahydrocannabinol; European Journal of Pharmacology. Volume 395, Issue, 21 Apr. 2000, Pages 1-7).

Several studies have shown that melatonin potentially enhances mitochondrial functioning in cells. An earlier hypothesis held that melatonin deficiency in the brain can cause mitochondrial dysfunction (Maurizi C P The mystery of Alzheimer's disease and its prevention by melatonin. Med Hypotheses. 1995 October; 45(4):339-40).

In 2000, Martin et al subsequently observed that melatonin prevented the inhibition of mitochondrial complexes I and IV induced by ruthenium red (Martin M., Macias M., Escames G., Reiter R. J., Agapito M. T., Ortiz G. G., Acuna-Castroviejo D. Melatonin-induced increased activity of the respiratory chain complexes I and IV can prevent mitochondrial damage induced by ruthenium red in vivo. J. Pinea. Res. 2000; 28:242-248.).

The above findings on melatonin with mitochondrial function was further confirmed by Mansouri and etal in the year 1999 further to demonstrate that melatonin protects against ethanol-induced hepatic mitochondrial DNA depletion in mice (Mansouri A., Gaou I., de Kerguenec C., Amsellem S., Haouzi D., Berson A., Moreau A., Feldmann G., Letteron P., Pessayre D., et al. An alcoholic binge causes massive degradation of hepatic mitochondrial DNA in mice Gastroenterology. 1999; 4.).

Melatonin treatment restores mitochondrial function in Alzheimer's mice: a mitochondrial protective role of melatonin membrane receptor signaling. (Dragicevic N, Copes N, O'Neal-Moffitt G, Jin J, Buzzeo R, Mamcarz M, Tan J, Cao C, Olcese J M, Arendash G W, Bradshaw P C J Pineal Res. 2011 August; 51(1):75-86; Mechanism of neuroprotection of melatonin against beta-amyloid neurotoxicity. Ionov M, Burchell V, Klajnert B, Bryszewska M, Abramov A Y Neuroscience. 2011 Apr. 28; 1800:229-37.).

Further, the studies outlined herein show that THC impairs mitochondrial functioning. Therefore the general expectation would be that THC combined with melatonin would lead to an impairment of mitochondrial functioning.

FIG. 14A and FIG. 14B demonstrate the opposite: the combination of ultra-low dose of THC and melatonin (CN-TRL, M1T2, M2T2 in FIG. 14A and FIG. 14B) enhances mitochondrial function in N2a/AβPPswe cells by almost 400% over the control.

The combination of ultra-low dose of THC and melatonin enhances mitochondrial function. The opposite would be expected if higher dose of THC is added to melatonin. The ultra-low dose of THC also allows for the reduction of melatonin dosing, which in turn reduces some of the side effects of melatonin.

Example 3: The Direct Effect of THC on Aβ Aggregation, One Pathological Marker of AD Additional hallmarks of AD pathology involve formation of Aβ aggregation.

In 2006 Eubanks and et al, demonstrated that THC competitively inhibits the enzyme acetylcholinesterase (AChE) as well as prevents AChE induced amyloid beta-peptide (Abeta) aggregation. The concentration used was 50 Eubanks's study indicate that 50 micro molar corresponds to 15.7 micro grams/ml. Therefore Eubanks dosing is in the range that causes psychological impairments. (Eubanks L M, et. al. A molecular link between the active component of marijuana and Alzheimer's disease pathology. Mol Pharm. 2006 November-December (36): 773-7.)

FIG. 3A shows that at ultra-low dose of THC, between 0.25 nM to 250 nM at the cell level, lowers Aβ aggregation. Further, at these low concentrations, which are about 20,000 times less than that used by Eubanks, there are no psychological impairments or significantly reduced psychological impairments such as acute panic, toxic delirium, paranoia, or mania among others.

Thus, ultra-low doses of THC inhibits Aβ aggregation, without any of the serious psychological impairments and serious side effects associated with larger doses of THC.

Example 4: The Effects of THC on the Phosphorylation of GSK3β

There is evidence that GSK3 plays a vital role in AD pathology. It has been associated with the buildup of amyloid-β plaque and the formulation of neurofibrillary tangles. GSK3 is implicated in directly promoting Aβ production, and is also implicated in hyperphosphorylation of tau proteins both hallmarks of seminal and sporadic AD. GSK3 activity is regulated by its own phosphorylation by other kinases. Phosphorylation of certain GSK3 residues can increase its ability to bind substrate, while phosphorylation of other sites can decrease its ability to bind substrate. For example, phosphorylation at tyrosine-216 in GSK3β or tyrosine-279 in GSK3α enhances the enzymatic activity of GSK3, while phosphorylation of serine-9 in GSK3β or serine-21 in GSK3α significantly decreases the active site availability.

A study by Ozaita et al 2007 demonstrated that THC increased phosphorylation of GSK3β, which results in decreasing GSK3β activity. Ozaita applied 10 mg/kg of body weight of THC to mice to demonstrate the results. (Ozaita Al, Puighermanal E, Maldonado R. Regulation of PI3K/Akt/GSK-3 pathway by cannabinoids in the brain. J Neurochem. 2007 August; 102(4):1105-14. Epub 2007 May 4.

We find that a different mechanism emerges from using ultra-low dosing of THC between 5,000 and 500,000 times less than that used by Ozaita, and about 4 times lower than the lowest FDA recommended dose. At these levels, THC decreases the phosphorylation of GSK3β, which in turn decreases GSK3β activity. As contrasted with Ozaita wherein a high dose of THC increases phosphorylation of GSK3β, which in turn decreases GSK3β activity Although, the end result, decreased GSK3β activity, is the same in both cases, the use of ultra-low dosing of THC is extremely important. High concentrations of THC as used by Ozaita results, as shown elsewhere, in severe psychological impairments such as acute panic, toxic delirium, paranoia, or mania.

Using ultra-low, dosing while achieving the same end point, decreased GSK3β activity, does not result in psychological impairments and is therefore an important pathway for treating plaques and tangles, the hallmarks of AD. Our results are shown in FIGS. 10A and 10B.

Example 5: The Effect of the Combination of THC and Melatonin on the Phosphorylation of GSK3β

A study by Hoppe showed that melatonin at a dose of 100 μM at the cellular level resulted in decreased GSK3β phosphorylation by about 40%. (J Pineal Res. 2010 April; 48(3):230-8. doi: 10.1111/j 0.1600-079X.2010.00747.x. Epub 2010 Jan. 28. Amyloid-beta neurotoxicity in organotypic culture is attenuated by melatonin: involvement of GSK-3beta, tau and neuroinflammation. Hoppe J B1, Frozza R L, Horn A P, Comiran R A, Bernardi A, Campos M M, Battastini A M, Salbego C.)

It has been found that ultra-low doses of THC added to melatonin achieves the result of decreased phosphorylation of GSK3β, by as about 40%. This is achieved at significantly lower dosage of melatonin, up to 10 times less than that used by Hoppe. A significantly lower dose of melatonin results in lowering side effects commonly associated with melatonin.

Thus, combining an ultra-low dose of THC and melatonin, results in decreased phosphorylation of GSK3β, at significantly lower doses of melatonin. A decreased dose of melatonin lowers the side effects commonly associated with melatonin intake like headache, dizziness, nausea, drowsiness depression, anxiety, tremor, camps, irritability, confusion, hypotension, among others. AD patients already suffer from many of these side effects, including anxiety, irritability, confusion, anxiety. A high dose of THC and a high dose of melatonin would only exasperate these symptoms, while lowering THC by as much as 100,000 times and melatonin by 10 times would not. The ratio of THC to melatonin where these desirable effects manifested are in the range of about 1:400: and about 1: 4,000.

Example 6: The Effect of THC on the Protein Expression of GSK3β

Alzheimer's disease research has not shown a connection between THC and the expression of GSK3β.

Prior studies make no connection between THC and the expression levels of GSK3β. It has been found that ultra-low doses of THC result in decreasing the expression of GSK3β substantially, by as much as 50% (FIG. 5A and FIG. 5B), over the untreated control. Lowering the expression of GSK3β is believed to have wide implications on many diseases including Alzheimer's disease.

Example 7: The Effect of THC and the Effect of the Combination of THC and Melatonin on the Phosphorylation of Tau and Tau Protein Expression In healthy neurons, tau binds and stabilizes microtubules. Hyperphosphorylation of tau leads to a reduced affinity with microtubules and the disturbance of the neuronal cytoskeleton, as well as resulting in resistance to proteolytic degradation and gradual accumulation in the cell body (Avila J. Tau aggregation into fibrillar polymers: taupathies. FEBS Lett 2000; 476: 82-92). The continuous aggregation of Aβ peptides along with hyperphosphorylation of the tau protein inside the cell, causing neurofibrillary tangle formation, are generally accepted as the major etiological factors of the neuronal cell death associated with the progression of AD (Octave, The amyloid peptide and its precursor in Alzheimer's disease. Rev Neurosci. 1995; 6: 287-316; Reitz, et al., Epidemiology of Alzheimer disease. Nat Rev Neurol. 2011; 7: 137-152; Pillay, et al., Molecular mechanisms, emerging etiological insights and models to test potential therapeutic interventions in Alzheimer's disease. Curr Alzheimer Res. 2004; 1: 295-306).

Earlier studies have demonstrated that Cannabidiol (CBD) a component of *Cannabis* inhibits beta-amyloid-induced tau protein hyperphosphorylation through the Wnt/beta-catenin pathway rescue in PC12 cells (Esposito et al., J Mol Med (Berl) 2006 March; 84(3):253-8). However, no studies have demonstrated the role of THC on phosphorylation of tau.

We demonstrate that ultra-low doses of THC (T1, T2, T3) lowers the phosphorylation of tau in a dose dependent manner (FIG. 6C, FIG. 6D, and FIG. 12). Similarly, we demonstrate that ultra-low dose of THC lowers the production of Tau (FIG. 12).

Earlier studies demonstrated that melatonin reduces tau phosphorylation induced by a series of activators of protein kinases and inhibitors of protein phosphatases. Several studies reported that melatonin efficiently attenuates tau or neurofilament hyperphosphorylation induced by wortmannin [Deng Y Q, Xu G G, Duan P, Zhang Q, Wang J Z. Effects of melatonin on wortmannin-induced tau hyperphosphorylation. Acta Pharmacol Sin 2005; 26: 519-26], calyculin A. [Li S P, Deng Y Q, Wang X C, Wang Y P, Wang J Z. Melatonin protects SH-SY5Y neuroblastoma cells from calyculin A-induced neurofilament impairment and neurotoxicity. J Pineal Res 2004; 36: 186-191] and okadaic acid [Wang Y P, Li X T, Liu S J, Zhou X W, Wang X C, Wang J Z. Melatonin ameliorated okadaic-acid induced Alzheimer-like lesions. Acta Pharmacol Sin 2004; 25: 276-80.] in N2a and SH-SY5Y neuroblastoma cells as we as in in-vivo studies (Wang D L, Ling Z Q, Cao F Y, Zhu L Q, Wang J Z. Melatonin attenuates isoproterenol-induced protein kinase A over activation and tau hyperphosphorylation in rat brain. J Pineal Res 2004; 37: 11-16.).

It has been found that certain combinations of melatonin with ultra-low dose THC (M1T2, M2T2) reduces phosphorylation of tau (FIG. 11C, FIG. 11D and FIG. 12).

Example 8. The Overall Effect of Ultra-Low Dose of THC Compared to Higher Doses of THC The current data shows in vitro anti-Aβ activity of THC in amyloidogenic N2a/AβPPswe cells, which occurs in a time- and dose-dependent manner, as seen in Table 2. Further, N2a/AβPPswe cells treated twice with THC, show an even greater reduction in Aβ levels at slightly higher concentrations.

TABLE 2

Difference and percent decrease of $A\beta_{40}$ (pg/ml) in THC-treated cells at 2.5 μg/ml compared with the control at different time points.

| Time Point | Control | THC 2.5 μg/ml | Percentage of decreased $A\beta_{40}$ |
|---|---|---|---|
| 6 hr | 1064.025 | 965.827 | 9.23% |
| 24 hr | 5303 | 3648.975 | 31.19% |
| 48 hr | 5935.525 | 2894.175 | 51.24% |

Studies using ThT assay, confirmed THC possesses anti-Aβ aggregate properties in a dose-dependent manner, suggesting possible intermolecular force interactions that prevent the molecular aggregation of Aβ peptides. ELISA was conducted to ensure the intermolecular interaction of THC with Aβ did not block the major B-cell epitope. The analysis indicated that regardless of the molecular interaction of THC with Aβ, an immune response should not be inhibited. The MTT assay confirmed that cells treated at efficacious concentration of THC showed no toxicity, suggesting such a treatment to be safe and effective for further experimentation in the AD animal model.

To date, no Aβ-specific therapeutic options for AD have been approved. While progression is being made in this field, rigorous efforts focus on developing compounds that can address or possess the inhibition of Aβ synthesis and anti-Aβ aggregation properties or characteristics that down regulate GSK-3β and pGSK-3β. The results demonstrate that THC possesses all of the above-mentioned properties. All of these areas address major etiological characteristics of AD. GSK-3β, pGSK-3β, and Aβ-plaque brain concentrations, the hallmark of AD, are major targets for current AD research. Furthermore, THC functions are pathway-dependent of the endogenous cannabinoid CB1 receptor recently discovered to possibly function in AD disease modulation by suppressing microglial activation upon receptor interaction. Notwithstanding, it should also be noted that low doses of THC are used to address the above-mentioned targets, thus avoiding risks induced by THC associated with memory impairment and risks associated with toxicity. In addition, low doses of THC can also enhance mitochondria function and has no negative drug interactions to melatonin, a potential therapeutic for AD.

The data shows a promising compound that addresses many major targets for AD therapeutics currently being research. THC, at an extremely low-dose level (2.5 nM), has the proclivity to slow or halt AD progression by dampening the synthesis of the major pathological marker of AD, Aβ. A potential mechanism responsible for the anti-pathological properties of THC with respect to AD was elucidated. Furthermore, both THC and caffeine, individually, have clearly exhibited lack of toxicity at low concentrations. In conclusion, the multifaceted functions of THC will ultimately decrease downstream tau hyperphosphorylation and neuronal death thereby halting or slowing the progression of this devastating disease. In the year 2006, Eubanks and et al, demonstrated that THC competitively inhibits the enzyme acetylcholinesterase (AChE) as well as prevents AChE induced amyloid beta-peptide (Abeta) aggregation. The concentration of THC used was 50 micromolar at the cellular level. We note that 50 micromolar corresponds to 15.7 micrograms/ml.

Figure 15:
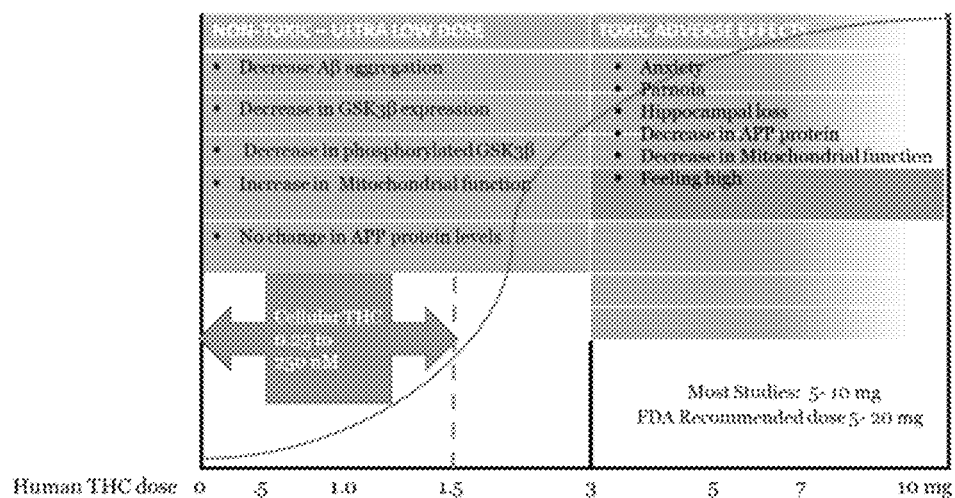
FIG. 15 is a schematic that shows the benefits of using ultra-low doses of THC as compared to higher doses of THC. The latter poses both behavioral and cellular toxic effects.

Based on the earlier preclinical and clinical investigations revealed that the higher doses of THC pose both behavioral and cellular toxic effects (FIG. 15).

As presented herein, ultra-low doses of THC result in a THC local concentration of 0.25 nM to 250 nM at the targeted cell(s). The doses presented herein are, for example, 20,000 times less than that used in the Eubanks study. Further, at these ultra-low levels, there are no psychological impairments such as acute panic, toxic delirium, paranoia, or mania. To put our findings in perspective, the dose considered in our study is about 20,000 times less than that used in the Eubanks study. The findings are summarized in FIG. 15 (see: Hoffman et al. 2007; Benford and Caplan 2011, and Eubanks L M, et. al. A molecular link between the active component of marijuana and Alzheimer's disease pathology. Mol Pharm. 2006 November-December (36): 773-7)

In the preceding specification, all documents, acts, or information disclosed do not constitute an admission that the document, act, or information of any combination thereof was publicly available, known to the public, part of the general knowledge in the art, or was known to be relevant to solve any problem at the time of priority.

The disclosures of all publications cited above are expressly incorporated herein by reference, each in its entirety, to the same extent as if each were incorporated by reference individually.

While there has been described and illustrated specific embodiments of a method of treating Alzheimer's disease and neurological disorders, it will be apparent to those skilled in the art that variations and modifications are possible without deviating from the broad spirit and principle of the present invention. It is also to be understood that the following claims are intended to cover all of the generic and specific features of the invention herein described, and all statements of the scope of the invention which, as a matter of language, might be said to fall there between.

What is claimed is:

1. A method for maintaining amyloid precursor protein level in a patient suffering from Alzheimer's disease, comprising administering tetrahydrocannabinol (THC) and melatonin to the patient, wherein the THC is administered in an ultra-low dose amount of from about 0.2 µg/kg to about 0.02 mg/kg of body weight of the patient and melatonin is administered in an amount from about 0.11 mg/kg to about 1.1 mg/kg of body weight of the patient, wherein Aß production and aggregation is concurrently decreased.

2. The method of claim 1 further comprising administering THC and melatonin at least one additional time at 6-hour intervals, 12-hour intervals, or 24-hour intervals.

3. The method of claim 1, wherein the THC is selected from the group consisting of organic THC, synthetic THC, Dronabinol, Δ9-THC, and THC-A.

4. An improved method for treating a patient having Alzheimer's disease with tetrahydrocannabinol (THC), the improvement comprising administering THC in an ultra-low dose amount of from about 0.2 µg/kg to about 0.02 mg/kg of body weight of the patient and melatonin in an amount from about 0.11 mg/kg to about 1.1 mg/kg of body weight of the patient, wherein the improvement maintains the patient's amyloid precursor protein levels while concurrently decreasing Aß production and aggregation.

* * * * *